United States Patent
Berrard et al.

(10) Patent No.: US 8,071,753 B2
(45) Date of Patent: Dec. 6, 2011

(54) RNAI MEDIATED EXPRESSION INHIBITION OF A CHOLINERGIC PROTEIN

(75) Inventors: Sylvie Berrard, Rueil Malmaison (FR); Marie José Lecomte, Paris (FR); Jacques Mallet, Paris (FR); Julie Santamaria, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 12/481,180

(22) Filed: Jun. 9, 2009

(65) Prior Publication Data

US 2010/0100978 A1    Apr. 22, 2010

Related U.S. Application Data

(60) Provisional application No. 61/059,886, filed on Jun. 9, 2008.

(51) Int. Cl.
*C07H 21/04* (2006.01)
*C07H 21/02* (2006.01)
*C12N 15/63* (2006.01)
*C12N 15/85* (2006.01)
*A61K 48/00* (2006.01)

(52) U.S. Cl. .................. 536/24.5; 536/23.1; 435/320.1; 435/325; 514/44

(58) Field of Classification Search .................. None
See application file for complete search history.

(56) References Cited

OTHER PUBLICATIONS

Inazu et al. (Journal of Neurochemistry, 2005, 94, pp. 1427-1437).*
Scherr et al. (Cell Cycle, 2:3, 251-257, 2003).*
Ziabreva et al. (Journal of Psychosomatic Research, 61, 2006, 311-316.*
Akkina et al. (J Virol., 1996, 70(4), 2581-5).*
Bierer et al., J. Neurochem. 64:749-760 (1995).
Schlieb et al., J. Neural Transm. 113:1625-1644 (2006).
Brandon et al., J. Neurosci. 23:539-549 (2003).
Brice et al., J. Neurosci. Res. 23:266-273 (1989).
Brummelkamp et al., Science 296:550-553 (2002).
Clark et al., . Journal of Neurochemistry 102:112-120 (2007).
Dykxhoorn et al., Nat. Rev. Mol. Cell Biol. 4:457-467 (2003).
Heckers et al., J Neurosci. 14:1271-1289 (1994).
McCann et al., Proceedings of the National Academy of Sciences of the United States of America 103:5149-5154 (2006).
Misgeld et al., Neuron 36:635-648 (2002).
Parent et al., Learning & Memory 11:9-20 (2004).
Waite et al., Life Sciences 58:1947-1953 (1996).
Walsh et al., Brain Research 702:233-245 (1995).
Wiley et al., Brain Research 562:149-153 (1991).
Wrenn et al., Brain Research 847:284-298 (1999).
Mallet et al., Acta Physiologica 191(Supp. 658):SW05-23 (2007), Abstract only.

* cited by examiner

*Primary Examiner* — Amy Bowman
(74) *Attorney, Agent, or Firm* — Don J. Pelto; Sheppard, Mullin, Richter & Hampton LLP

(57) ABSTRACT

The present invention relates to nucleic acid sequences producing at least one functional miRNA, at least one functional shRNA and/or at least one functional siRNA, said miRNA, shRNA or siRNA being designed to silence the expression of a gene that encodes a cholinergic protein. The present invention further relates to compositions and kits comprising such nucleic acid sequences as well as to uses thereof.

20 Claims, 9 Drawing Sheets

C)

D)

A) LV-ChAT-shRNA

B) LV-Sc-shRNA

SEQUENCE LISTING

<160> NUMBER OF SEQ ID NOS: 72

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ccugaagagc aguucaggau u                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uccugaacug cucuucaggu u                                              21

<210> SEQ ID NO 3
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gcacuuccaa gacaccaauu u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
auuggugucu uggaagugcu u                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cuggugugcu uagcuacaau u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uuguagcuaa gcacaccagu u                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gugaucuguu cacucaguuu u                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
aacugaguga acagaucacu u                                              21

<210> SEQ ID NO 9
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 9
uaaccggcau ggccauugau u                                              21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ucaauggcca ugccgguuau u                                              21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gagccaccug agauguucau u                                              21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ugaacaucuc agguggcucu u                                              21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gagcgagccu uguugacauu u                                              21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
augucaacaa ggcucgcucu u                                              21

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
```

-continued oligonucleotide
<220> FEATURE:
<223> OTHER INFORMATION: see specification as filed for detailed
      description of substitutions and preferred embodiments

<400> SEQUENCE: 15
cctgaagagc agttcaggat tcaagagatc ctgaactgct cttcaggttt tt            52

<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: see specification as filed for detailed
      description of substitutions and preferred embodiments

<400> SEQUENCE: 16
gcacttccaa gacaccaatt tcaagagaat tggtgtcttg gaagtgcttt tt            52

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: see specification as filed for detailed
      description of substitutions and preferred embodiments

<400> SEQUENCE: 17
ctggtgtgct tagctacaat tcaagagatt gtagctaagc acaccagttt tt            52

<210> SEQ ID NO 18
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: see specification as filed for detailed
      description of substitutions and preferred embodiments

<400> SEQUENCE: 18
gtgatctgtt cactcagttt tcaagagaaa ctgagtgaac agatcacttt tt            52

<210> SEQ ID NO 19
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: see specification as filed for detailed
      description of substitutions and preferred embodiments

<400> SEQUENCE: 19
taaccggcat ggccattgat tcaagagatc aatggccatg ccggttattt tt            52

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic

```
        oligonucleotide
<220> FEATURE:
<223> OTHER INFORMATION: see specification as filed for detailed
      description of substitutions and preferred embodiments

<400> SEQUENCE: 20
gagccacctg agatgttcat tcaagagatg aacatctcag gtggctcttt tt          52

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: see specification as filed for detailed
      description of substitutions and preferred embodiments

<400> SEQUENCE: 21
gagcgagcct tgttgacatt tcaagagaat gtcaacaagg ctcgctcttt tt          52

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ggcugaauga cauguaucuu u                                            21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
agauacaugu cauucagccu u                                            21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cugguguacu cagcuacaau u                                            21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uuguagcuga guacaccagu u                                            21

<210> SEQ ID NO 26
<211> LENGTH: 21
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gccucauuga caugagagau u                                              21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ucucucaugu caaugaggcu u                                              21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gagauguuca uggaugaaau u                                              21

<210> SEQ ID NO 29
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uuuauccaug aacaucucuu                                                20

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gagacuucuu cuagcaaguu u                                              21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
acuugcuaga agaagucucu u                                              21

<210> SEQ ID NO 32
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 32
gaccauucua gucagaaauu u                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
auuucugacu agaauggucu u                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ggcacccauu ggauauucuu u                                              21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
agaauaucca augggugccu u                                              21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gcucuacucu guggcauauu u                                              21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
auaugccaca gaguagagcu u                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 38
ccugacaaga augguauauu u                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
auauaccauu cuugucaggu u                                              21

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggccgaguau ugguuuauuu                                                20

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
auaaaccaau aucucggccu u                                              21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggccuuccuu gauguugauu u                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aucaacauca aggaaggccu u                                              21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 44
ggcaccaauu ggauauucuu u                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
agaauaucca auuggugccu u                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cugcugugca ugccaaauau u                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uauuuggcau gcacagcagu u                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ggccuuucau ugaucgcauu u                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
augcgaucaa ugaaaggccu u                                              21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
```

```
cacuguuacu ggacaacauu u                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51 auuugucca guaacagugu u                                               21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gcgauguguu gcuugaugau u                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ucaucaagca acacaucgcu u                                              21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
cuggacaaca uguuguacau u                                              21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uguacaacau guuguccagu u                                              21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
cgcuguuacu ggacaacauu u                                              21
```

-continued

```
<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
auguugucca guaacagcgu u                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gccuucauua gcuucggaau u                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uuccgaagcu aaugaaggcu u                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gaggacgacu acaacuacuu u                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aguaguugua gucguccucu u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gacgacuaca acuacuacuu u                                              21

<210> SEQ ID NO 63
```

-continued

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
aguaguaguu guagucgucu u                                                  21

<210> SEQ ID NO 64
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64 ttcaagaga                                                                 9

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ucgucauagc gugcauaggu u                                                  21

<210> SEQ ID NO 66
<211> LENGTH: 19
<212> TYPE: RNA
<213> ORGANISM: Unknown
<220> FEATURE:
<223> OTHER INFORMATION: Description of Unknown: Rat or
      Mouse oligonucleotide

<400> SEQUENCE: 66
ccugaagagc aguucagga                                                     19

<210> SEQ ID NO 67
<211> LENGTH: 19
<212> TYPE: RNA
<213> ORGANISM: Unknown
<220> FEATURE:
<223> OTHER INFORMATION: Description of Unknown: Rat or
      Mouse oligonucleotide

<400> SEQUENCE: 67
gcacuuccaa gacaccaau                                                     19

<210> SEQ ID NO 68
<211> LENGTH: 19
<212> TYPE: RNA
<213> ORGANISM: Unknown
<220> FEATURE:
<223> OTHER INFORMATION: Description of Unknown: Rat or
      Mouse oligonucleotide

<400> SEQUENCE: 68
cuggugugcu uagcuacaa                                                     19

<210> SEQ ID NO 69
<211> LENGTH: 19
<212> TYPE: RNA
```

```
<213> ORGANISM: Unknown
<220> FEATURE:
<223> OTHER INFORMATION: Description of Unknown: Rat or
      Mouse oligonucleotide

<400> SEQUENCE: 69
gugaucuguu cacucaguu                                             19

<210> SEQ ID NO 70
<211> LENGTH: 19
<212> TYPE: RNA
<213> ORGANISM: Unknown
<220> FEATURE:
<223> OTHER INFORMATION: Description of Unknown: Rat or
      Mouse oligonucleotide

<400> SEQUENCE: 70
uaaccggcau ggccauuga                                             19

<210> SEQ ID NO 71
<211> LENGTH: 19
<212> TYPE: RNA
<213> ORGANISM: Unknown
<220> FEATURE:
<223> OTHER INFORMATION: Description of Unknown: Rat or
      Mouse oligonucleotide

<400> SEQUENCE: 71
gagccaccug agauguuca                                             19

<210> SEQ ID NO 72
<211> LENGTH: 19
<212> TYPE: RNA
<213> ORGANISM: Unknown
<220> FEATURE:
<223> OTHER INFORMATION: Description of Unknown: Rat or
      Mouse oligonucleotide

<400> SEQUENCE: 72
gagcgagccu uguugacau                                             19
```

RNAI MEDIATED EXPRESSION INHIBITION OF A CHOLINERGIC PROTEIN

CROSS REFERENCE TO RELATED APPLICATIONS

This application claims the benefit, under 35 U.S.C. §119, of provisional U.S. Application Ser. No. 61/059,886, filed Jun. 9, 2008, the entire contents and substance of which is hereby incorporated by reference.

FIELD OF THE INVENTION

The present invention relates to the field of biology, nervous system diseases, and gene therapy. More particularly, the invention relates to methods and compositions for modulating (e.g. reducing or inhibiting) the expression of a gene encoding a cholinergic protein, in particular the choline acetyltransferase (ChAT) which is the enzyme of acetylcholine biosynthesis. Generally, the present invention involves the use of a viral vector, in particular a lentiviral vector comprising a lentiviral genome comprising a nucleic acid sequence producing at least one functional micro RNA (miRNA), at least one functional short-hairpin RNA (shRNA) and/or at least one functional small interfering RNA (siRNA), preferably derived from said shRNA, said miRNA, shRNA and siRNA being designed to silence the expression of a gene that encodes a cholinergic protein, in particular the choline acetyltransferase (ChAT), into cells of the nervous system.

BACKGROUND

Cholinergic neurons are involved in numerous physiological functions in mammals including motor activity, sleep-wakefulness (vigilance) and cognitive behavior (cognition). The dramatic consequences of the loss of cholinergic neurons which innervate the hippocampus and the cerebral cortex, associated with Alzheimer's disease, are evidence of the importance of these neurons for normal behavior (Bierer et al., 1995). Impairment of the cholinergic system has been also reported in other pathologies, for example in certain forms of epilepsy and in schizophrenia (Holt et al., 1999; Friedman et al., 2007).

One way to investigate the function of cholinergic structures is to analyze the consequences of their impairment. Until recently, the generation of such a loss-of-function phenotype relied on the destruction of cholinergic neurons by methods which are not specific for these neurons (excitotoxins, electrolytic lesions).

The immunotoxin 192IgG-saporin is a more selective tool to deplete cholinergic neurons of the basal forebrain (Wiley et al., 1991; Waite et al., 1996; Wrenn et al., 1999), but when delivered by intracerebroventricular injection, it can also affect other cell populations expressing the p75 neurotrophin receptor, including the cerebellar Purkinje cells (Heckers et al., 1994; Walsh et al., 1995).

Another approach to generate cholinergic deficits is to inactivate specifically the cholinergic neurons in given nuclei. This strategy has the advantage of sparing the neurons and affecting only cholinergic neurotransmission. This can be achieved by inhibiting locally the expression of a protein required for cholinergic presynaptic function. Conditional gene knockout requires the slow and costly generation of mice with loxP sites and is restricted to date to this animal species. Constitutive knockout of the ChAT gene in the mouse is further lethal at birth and thus cannot be used to investigate cholinergic function in the adult (Brandon et al., 2003; Misgeld et al., 2002).

Inventors herein provide new and powerful tools that are able to achieve effective and specific inhibition of choline acetyltransferase expression which can be spatially and/or timely controlled. The method according to the present invention now obviates the generation of knock-out mice and further allows studies in species other than the mouse.

The present invention allows for the first time inactivation of cholinergic neurotransmission, without destroying cholinergic structures, using a viral vector, in particular a lentiviral vector which can efficiently transduce cells of the nervous system and specifically modulate (e.g., down-regulate or inhibit) the synthesis or expression of a presynaptic cholinergic protein, in particular of the choline acetyltransferase (ChAT), in these cells, through RNA interference (RNAi). Other presynaptic cholinergic proteins required for cholinergic function include the high affinity choline transporter (CHT1) and the vesicular acetylcholine transporter (VAChT).

The products of the invention, in particular the nucleic acid sequences and viruses, in particular lentiviruses, are new cholinergic antagonists which are, in particular, able to inhibit specifically ChAT synthesis in cells which produce acetylcholine in vitro, ex vivo or in vivo. Examples of cells producing acetylcholine are cells of the nervous system, in particular cholinergic neurons of the Central Nervous System (CNS), or cells of the Peripheral Nervous System (PNS) such as neurons located in the intestine. Cells producing acetylcholine may further be non neuronal cells such as lymphocytes or more generally cells located in the blood or in the placenta.

Using such a nucleic acid or virus, it is now possible to study the particular role of cholinergic nuclei in the brain and, more generally, the functional anatomy of the cholinergic system. The present invention indeed allows the persistent or long-term, and preferably spatially restricted, suppression of the effects of a particular cholinergic protein, as defined previously, which inactivates the cholinergic neurotransmission. Using in particular modified lentiviral vectors allows timed and thus temporary and reversible ChAT suppression.

Thanks to the herein described virus vectors, it is also possible to develop new animal models (in particular rat and mouse animal models) of brain disorders or of nervous system diseases, without being compromised by serious unwanted side effects as seen in the past due to the lack of specificity of the methods of lesion which destroyed the whole structures containing the cholinergic neurons. Using the tools and methods herein described, it is possible to identify molecular networks regulated by cholinergic neurotransmission.

The screening of new drugs as well as the development of safe and efficient prophylactic or therapeutic strategies are also now possible using said tools and methods.

SUMMARY OF THE INVENTION

Inventors have now discovered that it is possible to specifically, efficiently, stably and safely silence the expression of genes encoding presynaptic cholinergic proteins, in particular the gene that encodes choline acetyltransferase (ChAT), and thereby inhibit acetylcholine synthesis and inactivate cholinergic neurotransmission, in vitro in cultured cells or in vivo, in defined brain areas of a subject, without deteriorating cells, in particular cholinergic neurons.

The present invention relates to compounds, compositions, and methods useful for modulating the expression and activity of a presynaptic cholinergic protein by RNA interference (RNAi) using small nucleic acid molecules, such as micro RNA (miRNA), short-hairpin RNA (shRNA) and/or short or small interfering RNA (siRNA), as specified in the attached claims, incorporated herein by reference. These compounds and compositions constitute new and highly specific cholinergic antagonists.

It is indeed herein demonstrated that RNA interference (RNAi) constitutes a powerful tool to efficiently and specifically silence, on the post-transcriptional level, the synthesis or expression of a presynaptic cholinergic protein. Herein described are efficient interfering sequences and viral vectors, in particular lentiviral vectors, designed to reach this aim in a safe and controlled manner.

The present disclosure in particular provides a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes a cholinergic protein.

The disclosure further provides a virus vector, in particular a lentivirus, capable of generating a loss-of-function phenotype, comprising a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes a cholinergic protein. The virus vector is preferably selected from the group consisting of a lentivirus, an adenovirus, an adenovirus associated virus, and an herpes simplex virus.

A particular non replicative lentivirus herein described comprises a lentiviral genome comprising a nucleic acid sequence producing at least one functional miRNA, at least one functional shRNA and/or at least one functional siRNA, preferably derived from said shRNA, said miRNA, shRNA and siRNA being designed to silence the expression of a gene that encodes a presynaptic cholinergic protein, in particular choline acetyltransferase (ChAT), said lentivirus being preferably pseudotyped for the selective transfer of the lentiviral genome into cells of the nervous system, in particular into cells of the central nervous system (CNS), preferably in cholinergic neurons, or into cells of the peripheral nervous system (PNS).

The disclosure also provides a recombinant cell comprising a nucleic acid or a virus vector as herein described, an animal, in particular a non human animal, comprising a nucleic acid, a virus vector or a recombinant cell as herein described, as well as compositions, in particular pharmaceutical compositions, comprising one or more of the herein described nucleic acids, virus vectors or cells, and optionally a pharmaceutically acceptable carrier or excipient. In addition, the pharmaceutical compositions may be employed in conjunction with other therapeutic compounds.

The disclosure also provides a method for silencing the expression of a gene that encodes a cholinergic protein in an animal, comprising administering to said animal a composition comprising a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes said cholinergic protein.

A method for modulating (e.g. decreasing or suppressing) expression of a gene that encodes a cholinergic protein, such as ChAT, in a cell, the method comprising the steps of:

introducing into the cell a miRNA, a siRNA, a shRNA or a viral vector, according to the present invention, preferably a lentiviral vector comprising a lentiviral genome comprising a nucleic acid sequence producing at least one functional miRNA, at least one functional short-hairpin RNA (shRNA) and/or at least one functional siRNA, preferably derived from said shRNA, said miRNA, shRNA and siRNA being designed to silence the expression of the gene that encodes a presynaptic cholinergic protein, said lentivirus being preferably pseudotyped for the selective transfer of the lentiviral genome into cells of the nervous system, and placing the cell under conditions wherein the RNA specific for the gene is expressed in an amount sufficient to cause a detectable decrease in expression of the gene.

The disclosure further provides a method of screening compounds in vivo in an animal model or ex vivo in cultured animal cells, preferably cultured human cells, comprising the identification or selection of a compound allowing or enhancing the synthesis of acetylcholine or of a compound compensating an acetylcholine deficit by acting either on the cholinergic neurons themselves or on the target cells of said cholinergic neurons.

Also provided are methods of preventing or treating a nervous system (NS) disorder or of alleviating the symptoms thereof, in a subject or animal, preferably a mammal, more preferably a human, said methods comprising administering to said subject a cholinergic antagonist as herein described, and preferably a pharmaceutically acceptable carrier or excipient.

In another aspect, the present disclosure provides a kit comprising any one of the herein-described nucleic acids, viruses or compositions, and a notice comprising instructions for using the corresponding product.

Typically, the kit is a kit for expressing a nucleic acid designed to silence the expression of a gene encoding a cholinergic protein, comprising a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes said cholinergic protein, and a notice comprising instructions for using the nucleic acid sequence.

A particular kit comprises at least one lentivirus according to the present invention. Generally, the kit also comprises one or more containers filled with one or more of the ingredients of the pharmaceutical compositions of the invention. Associated with such container(s) can be a notice providing instructions for using the lentivirus or compositions according to the present methods.

c) miRNA pathway. DICER also cleaves the ~70 nucleotides hairpin miRNA precursor to produce ~22 nucleotides miRNA.

Figure 2:
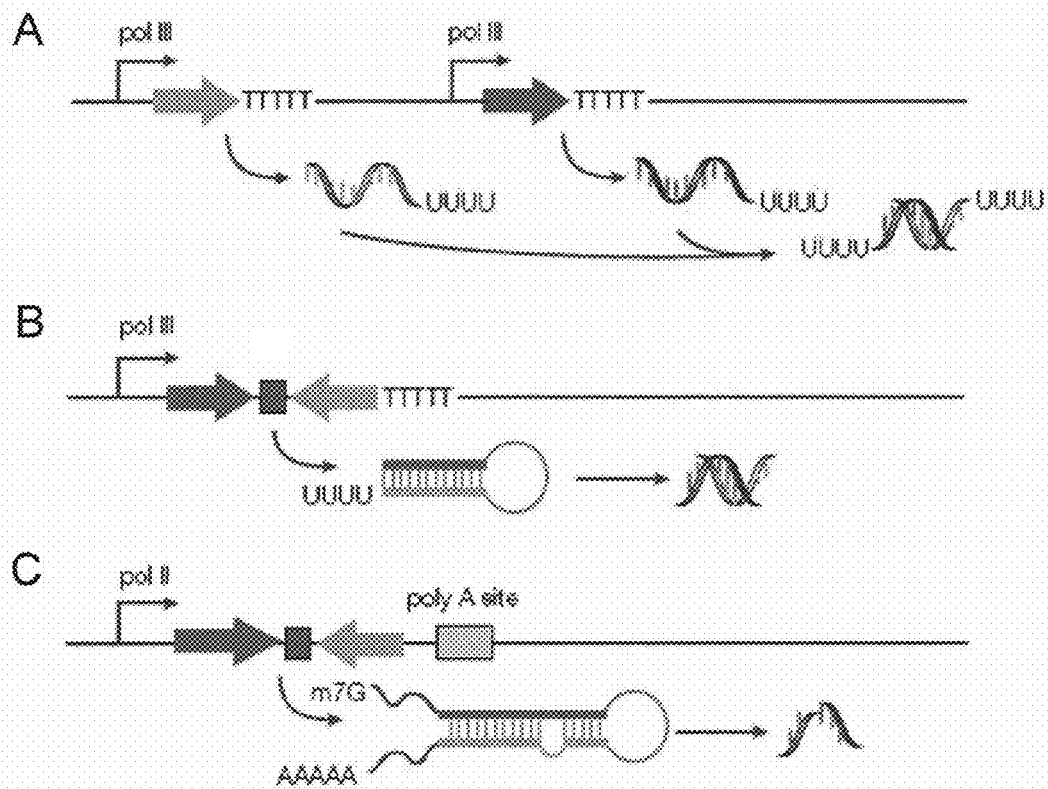
Figure 3:
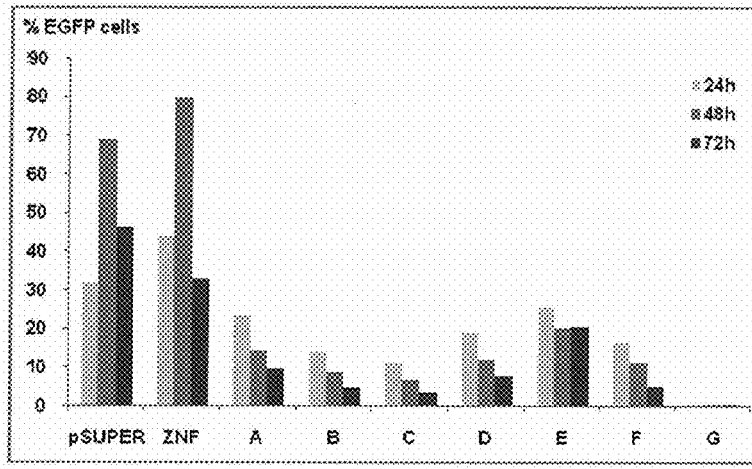
Figure 3:
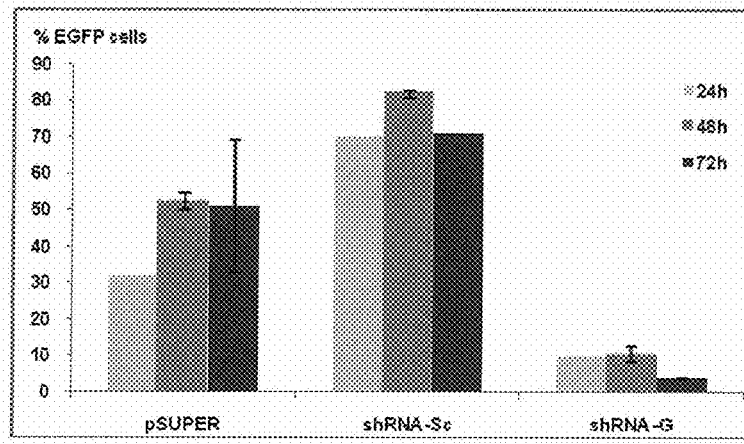
Figure 3:
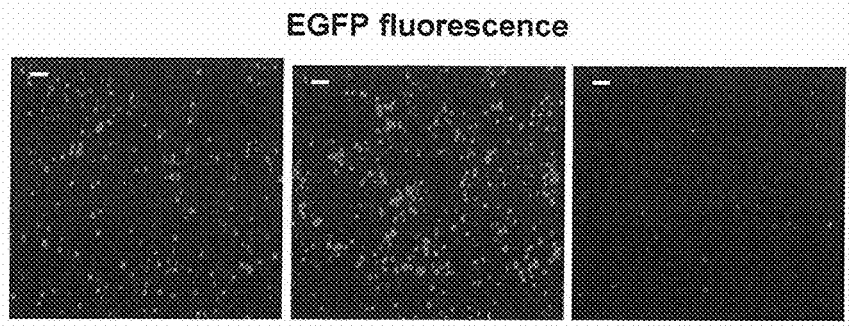
Figure 4:
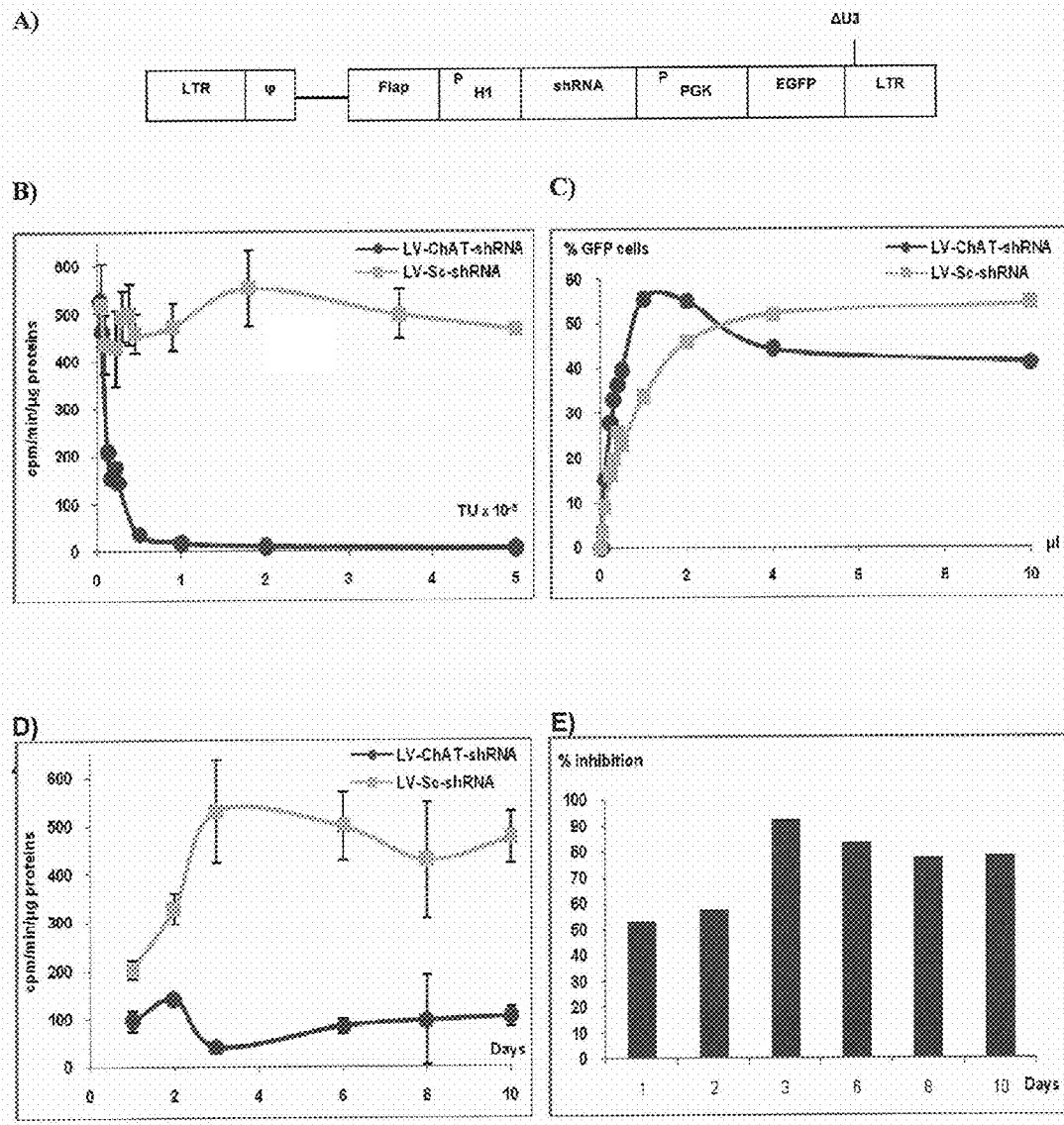

FIG. 2: Methods to generate siRNAs in vivo from plasmidic or viral vectors
A) sense and antisense strands of the siRNA are expressed from tandem polIII promoters
B) short hairpin RNA (shRNA) is expressed from a singe polIII promoter
C) Imperfect duplex hairpin, based on pre-miRNA is expressed from polII promoter and is processed by DICER into a mature miRNA FIG. 3: Screening of shRNAs for silencing an EGFP-ChAT fusion protein
293T cells were co-transfected with the EGFP-ChAT plasmid and either the pSUPER plasmid without an insert or the indicated pSUPER constructs producing the shRNA-A to -G or the scrambled sequence (shRNA-Sc). A shRNA specific for the ZNF-191 protein (ZNF) was also used as a negative hairpin control.
(A, C) Results are expressed as the percentage of fluorescent cells, determined 24 h, 48 h and 72 h after transfection. Data in C) are representative of 3 independent experiments performed in duplicate. Bars represent SEM.
(B) Percentages of inhibition of EGFP fluorescence by each pSUPER construct calculated relative to the fluorescence with the pSUPER vector.
(D) Visualization of EGFP fluorescence in cells transfected with either the control empty pSUPER or the pSUPER plasmids expressing the scrambled sequence or the shRNA-G. Scale bars: 2 mm FIG. 4: Knockdown of endogenous ChAT expression by lentiviral-vector-mediated RNAi in NG108-15 cells
(A) Schematic representation of the lentiviral construct for inhibition of ChAT expression. LTR (long terminal repeats), ψ (packaging sequence) and the central Flap element are sequences derived from HIV-1. The ChAT-shRNA-G or the scrambled RNA are produced under the control of the H1 promoter (P H1). EGFP expression is directed by the PGK promoter (P PGK).
(B, C) Dose-dependent reduction of ChAT expression. Cells ($8 \times 10^4$) were transduced with various amounts (0.05 to 10 μl) of lentiviral vectors (LV-ChAT-shRNA) (titer: $9 \times 10^7$ TU/ml) or LV-Sc-shRNA (titer: $5 \times 10^7$ TU/ml).
B) ChAT activity was measured 10 days post-infection. Data are expressed as mean±SEM.
C) The proportion of cells that were fluorescent was determined in sister cultures.
(D, E) Time course analysis of lentiviral-mediated ChAT knockdown. Cells ($8 \times 10^4$) were transduced with $13.5 \times 10^4$ TU of either (LV-ChAT-shRNA or LV-Sc-shRNA).
D) ChAT activity was determined between 1 and 10 days post-infection. Values represent means±SEM.
E) Inhibition of ChAT expression in (LV-ChAT-shRNA) transduced cells was calculated relative to the ChAT activity in cells transduced with the control LV-Sc-shRNA vector.

Figure 5:
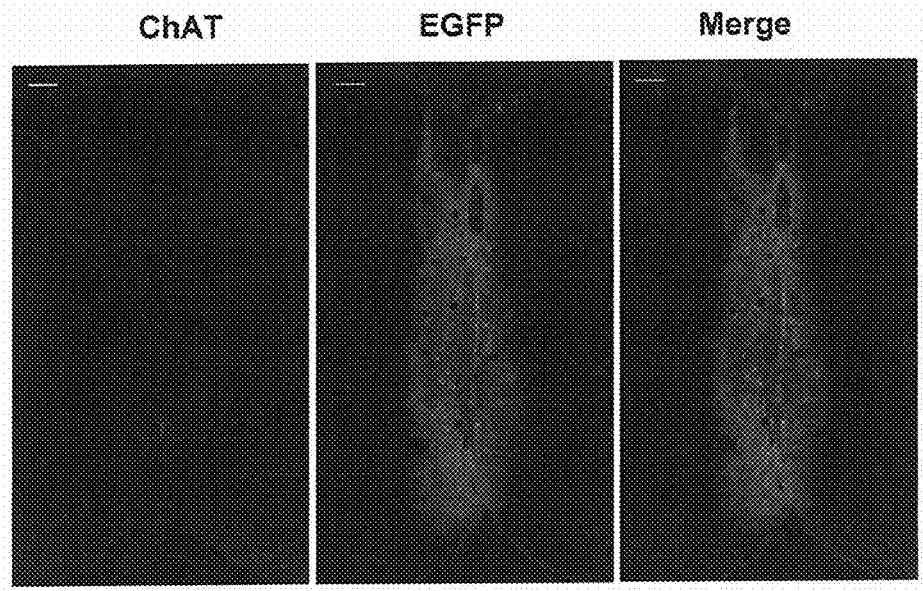
Figure 5:
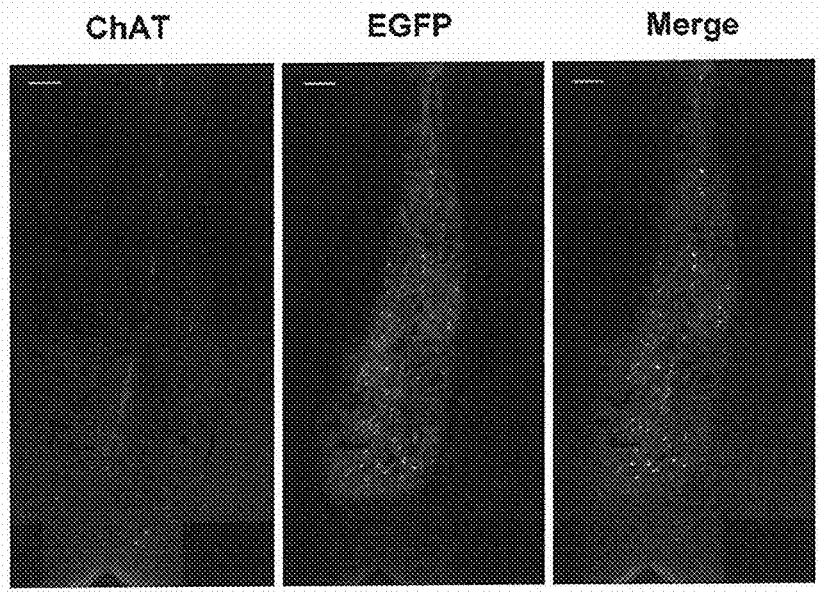
Figure 5:
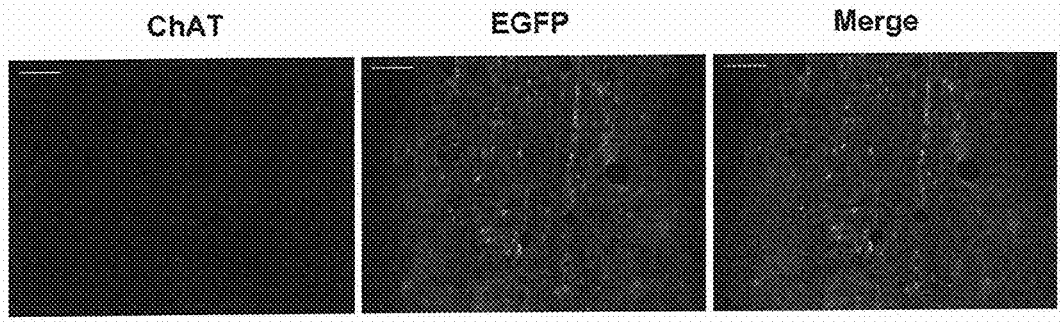
Figure 5:
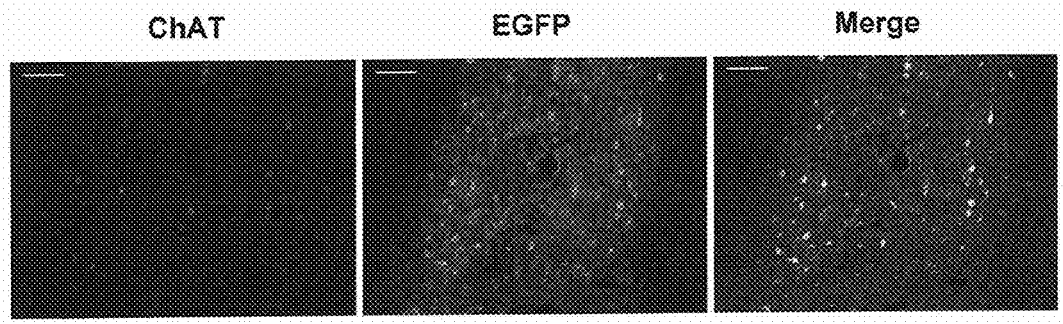
Figure 5:
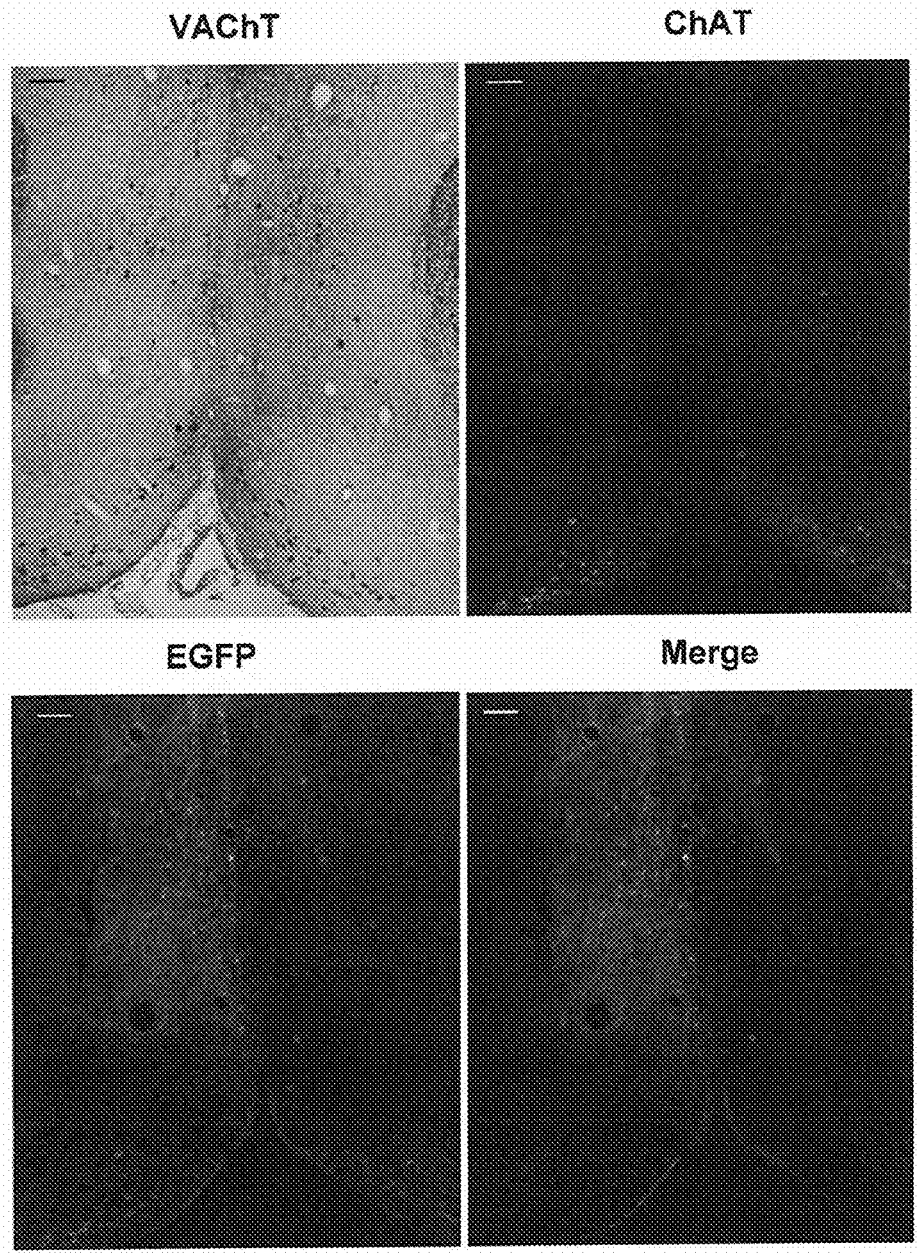

FIG. 5: Down regulation of ChAT protein in LV-ChAT-shRNA-infected medial septum.
(A-D) Fluorescent immunostaining for EGFP and ChAT two weeks after stereotaxic injection of LV-ChAT-shRNA (A,C) or LV-Sc-shRNA (B,D) into the MS.
(A, B) Photomontages of the MS area.
(C and D): High magnification views of MS infected neurons shown in panels A) and B), respectively.
EGFP labeling shows the transduced cells. ChAT and EGFP were co-localized in LV-Sc-shRNA infected neurons (B,D) as indicated by arrows but not in LV-ChAT-shRNA infected neurons in which ChAT immunoreactivity is clearly lost (A,C).
(E) Immunostaining of VAChT and ChAT/EGFP in adjacent MS sections two weeks after injection with LV-ChAT-shRNA (photomontages). Note the loss of ChAT immunoreactivity while that of VAChT is detected in the MS area.
Scale bars: 200 μm (A,B); 100 μm (C,D,E).

DETAILED DESCRIPTION OF THE INVENTION

Definitions

In describing, exemplifying and claiming the present invention, the following terminology will be used in accordance with the definitions set out below. Where not otherwise indicated, the terms are intended to have the meaning generally recognized in the art.

By choline acetyltransferase (ChAT) is meant ChAT peptide or protein or a naturally occurring fragment thereof, wherein the peptide or protein is encoded by the ChAT gene.

By vesicular acetylcholine transporter (VAChT) is meant VAChT peptide or protein or a naturally occurring fragment thereof, wherein the peptide or protein is encoded by the VAChT gene.

By high-affinity choline transporter (CHT1) is meant CHT1 peptide or protein or a naturally occurring fragment thereof, wherein the peptide or protein is encoded by the CHT1 gene.

By "RNA" is meant a molecule comprising at least one ribonucleotide residue. By "ribonucleotide" is meant a nucleotide with a hydroxyl group at the 2' position of a-D-ribofuranose moiety. The terms include double-stranded RNA, single-stranded RNA, isolated RNA such as partially purified RNA, essentially pure RNA, synthetic RNA, recombinantly produced RNA, as well as comprising non-standard nucleotides, such as non-naturally occurring nucleotides or chemically synthesized nucleotides or deoxynucleotides.

The terms "short-hairpin RNA", "shRNA", "short interfering nucleic acid", "siRNA", "small interfering RNA" or "short interfering RNA", "short interfering nucleic acid molecule", "short interfering oligonucleotide molecule", "miRNA", "micro RNA" as used herein refer to any nucleic acid molecule capable of mediating RNA interference "RNAi" or gene silencing in a sequence-specific manner.

Figure 1:
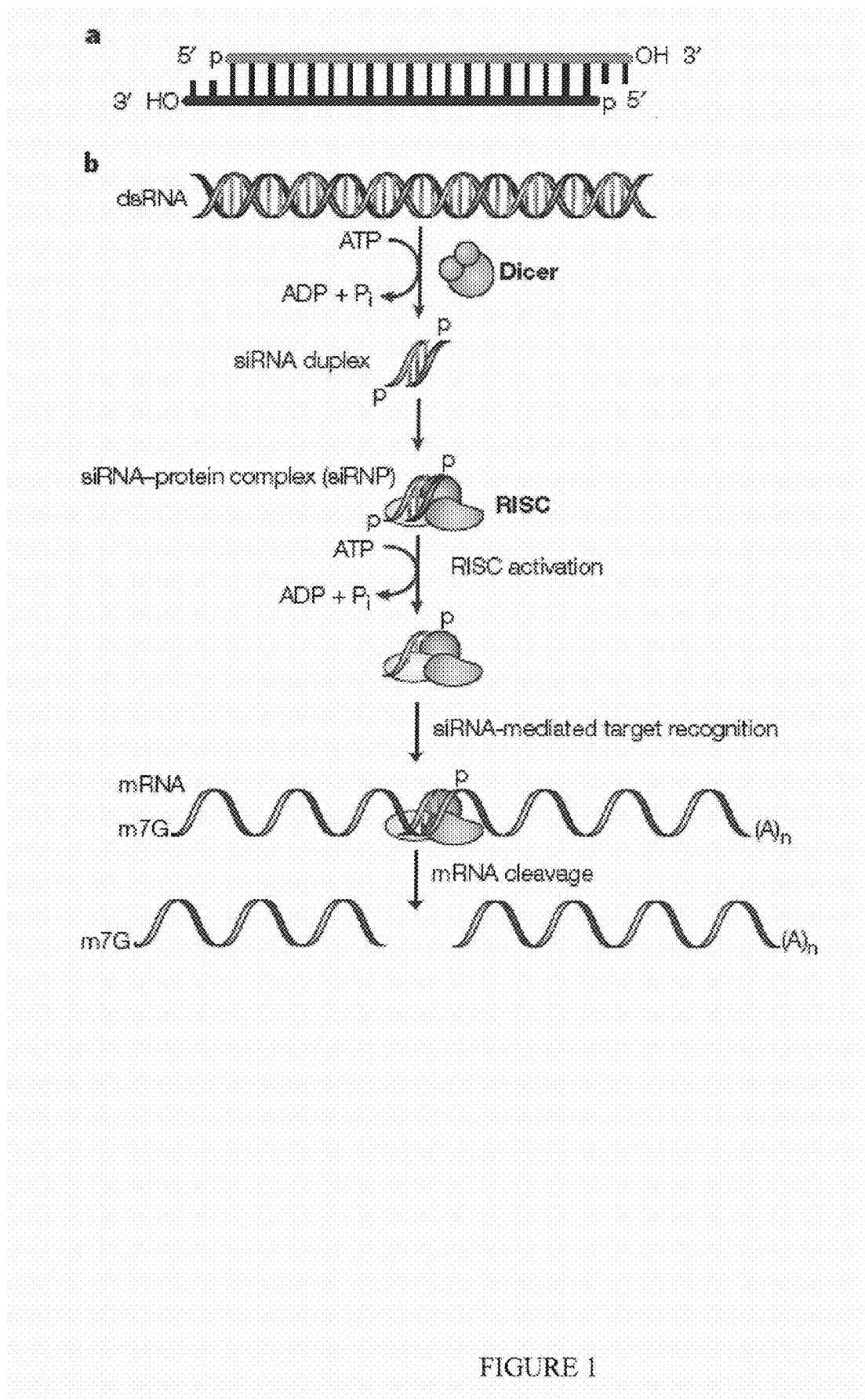
FIG. 1: RNA interference pathways (from Dykxhoorn et al., 2003)
a) Structure of a small interfering RNA (siRNA). The molecular structure of a siRNA includes 5' phosphorylated ends, a 19 to 22 nucleotides duplexed region and 2 nucleotides unpaired and unphosphorylated 3' ends that are characteristic of RNAse III cleavage products.
b) siRNA pathway. In an initiation phase, double stranded RNA (dsRNA) is cleaved by the enzyme DICER, giving rise to siRNA duplex. In an activation phase, the siRNA duplex is associated to the enzymatic complex that leads to recognition of the mRNA target and enzymatic degradation of the mRNA target.
Figure 1:
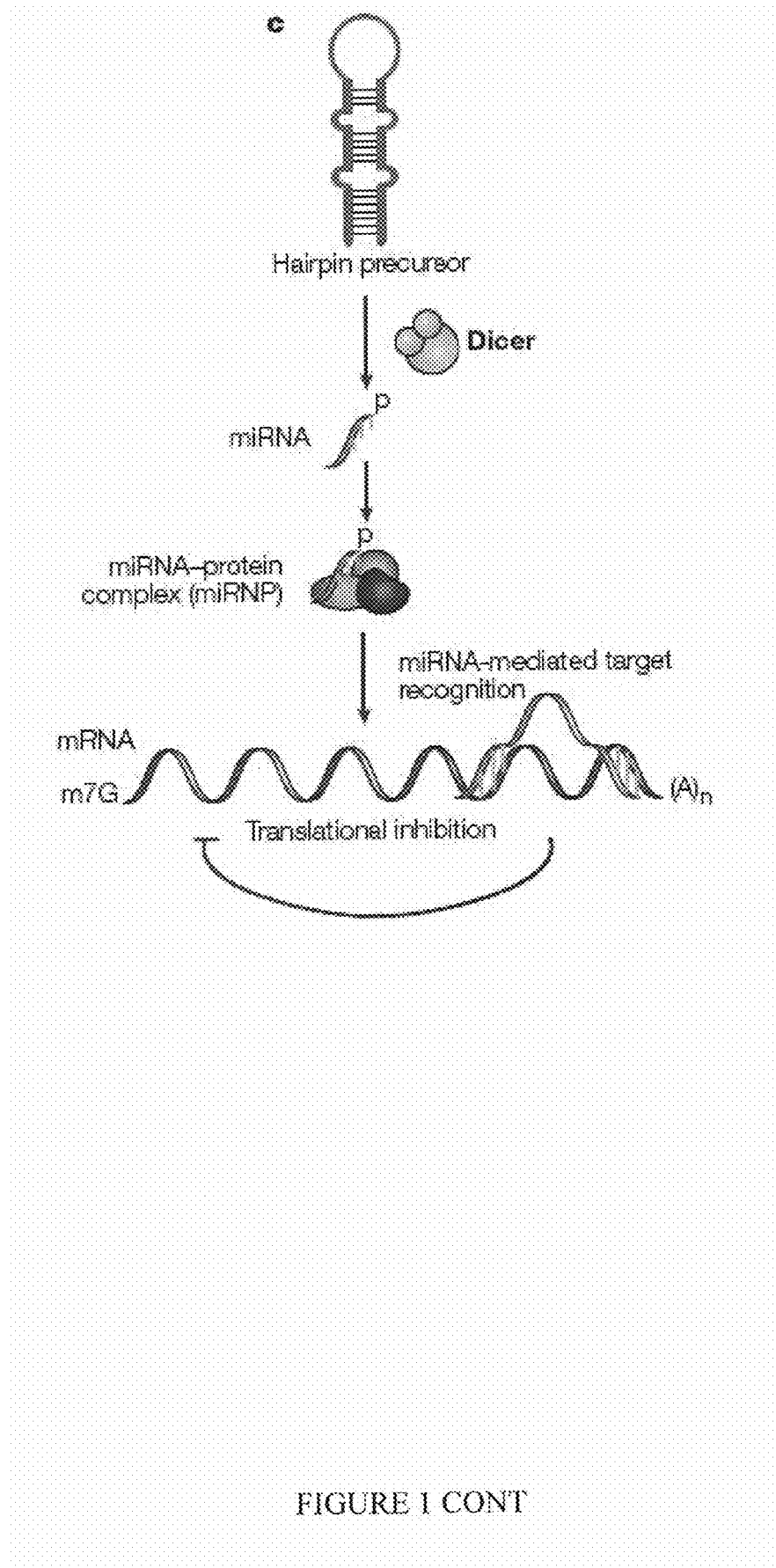

RNA interference (RNAi) describes a process wherein double-stranded RNA (dsRNA), when present inside a cell, inhibits expression of an endogenous gene that has an identical or nearly identical sequence to that of the dsRNA. Inhibition is caused by the specific degradation of the messenger RNA (mRNA) transcribed from the target gene. In greater detail, RNA interference describes a process of sequence-specific post-transcriptional gene silencing in animals mediated by the expression of "small interfering RNAs" (siRNAs) after in situ cleavage (Brummelkamp et al., 2002). The initial basic process involves double stranded RNA (dsRNA) that is/are processed by cleavage into shorter units (the so called siRNA) that guide recognition and targeted cleavage of homologous target messenger RNA (mRNA) (see FIG. 1a).

The method does not require the time-consuming genetic manipulations needed for classical gene knock-out strategies and has therefore emerged as a valuable tool in molecular genetics that may also be applied to human therapy.

The currently known mechanism of RNAi can be described as follows:

The processing of dsRNA into siRNAs, which in turn induces degradation of the intended target mRNA, is a two-step RNA degradation process. The first step involves a dsRNA endonuclease (ribonuclease III-like; RNase III-like) activity that processes dsRNA into smaller sense and antisense RNAs which are most often in the range of 21 to 25 nucleotides (nt) long, giving rise to the so called small interfering RNAs (siRNAs). This RNase III-type protein is termed "Dicer". In a second step, the antisense siRNAs produced combine with, and serve as guides for, a different ribonuclease complex called RNA-induced silencing complex (RISC), which allows annealing of the siRNA and the homologous single-stranded target mRNA, and the cleavage of the target homologous single-stranded mRNAs. Cleavage of the target mRNA has been observed to place in the middle of the duplex region complementary to the antisense strand of the siRNA duplex and the intended target mRNA (see FIG. 1b) (Dykxhoorn et al., 2003 for review).

Micro RNAs (miRNAs) constitute non coding RNAs of 21 to 25 nucleotides, which controls gene expression at post-transcriptional level. miRNAs are synthesized from ARN polymerase II or ARN polymerase III in a pre-miRNA of 125 nucleotides. Pre-miRNA are cleaved in the nucleus by the enzyme Drosha, giving rise to a precursor called imperfect duplex hairpin RNA (or miRNA-based hairpin RNA). These imperfect duplex hairpin RNAs are exported from the nucleus to the cytoplasm by exportin-5 protein, where it is cleaved by the enzyme DICER, giving rise to mature miRNAs. miRNAs combine with RISC complex which allows total or partial annealing with the homologous single-stranded target mRNA. Partial annealing with the mRNA leads to the repression of protein translation, whereas total annealing leads to cleavage of the single-stranded mRNA (see FIG. 1c; Dykxhoorn et al., 2003 for review).

At least three methods to generate RNAi-mediated gene silencing in vivo are known and usable in the context of the present invention (Dykxhoorn et al., 2003 for review):

siRNAs with a single sequence specificity can be expressed in vivo from plasmidic or viral vectors using:

Tandem polymerase III promoter that express individual sense and antisense strands of the siRNAs that associate in trans (see FIG. 2A)

a single polymerase III promoter that expresses short hairpin RNAs (shRNAs) (see FIG. 2B)

a single polymerase II promoter that expresses an imperfect duplex hairpin RNA (pre-miRNA) which is processed by DICER giving rise to a mature miRNA (see FIG. 2C).

By "antisense strand" is meant a nucleotide sequence of a siRNA molecule having complementarity to a sense region of the siRNA molecule. In addition, the antisense strand of a siRNA molecule comprises a nucleic acid sequence having complementarity with a target nucleic acid sequence.

By "sense strand" is meant a nucleotide sequence of a siRNA molecule having complementarity to an antisense region of the siRNA molecule.

By "modulate" and "modulation" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" and within the scope of the invention, the preferred form of modulation is inhibition but the use of the word "modulate" is not limited to this definition.

By "inhibit", "silence" or "down regulate" it is meant that the levels of expression product or level of RNAs or equivalent RNAs encoding one or more gene products is reduced below that observed in the absence of the nucleic acid molecule of the invention. In one embodiment, inhibition with a nucleic acid molecule capable of mediating RNA interference (siRNA, shRNA, miRNA) preferably is below that level observed in the presence of an inactive or attenuated molecule that is unable to mediate an RNAi response.

By "target protein" is meant any protein whose expression or activity is to be modulated. Preferred target proteins are presynaptic cholinergic proteins.

By "target nucleic acid" or "target gene" is meant any nucleic acid sequence whose expression or activity is to be modulated. The target nucleic acid can be DNA or RNA. In the context of the invention, the "target gene" is a gene that encodes a presynaptic cholinergic protein.

By "subject" is meant an organism, preferably an animal organism, which is a donor or recipient of explanted cells or the cells themselves. "Subject" also refers to an organism to which the nucleic acid molecules of the invention can be administered. The subject may be a non-human animal, preferably a mammal. The subject may also be a human subject.

New Approach for Cholinergic Neurotransmission Inactivation:

The present disclosure provides a novel strategy of efficient and stable cholinergic neurotransmission inactivation based on the neutralization, via RNA interference, of the mRNAs which encode proteins responsible for the production of acetylcholine, without deteriorating cells producing acetylcholine, in particular cholinergic neurons. Such a protein responsible for the production of acetylcholine is in particular the choline acetyltransferase (ChAT) protein, which is responsible for the conversion of choline and acetyl-CoA into acetylcholine.

Inventors herein demonstrate that said cholinergic proteins, in particular presynapticcholinergic proteins, are appropriate and valuable targets in the context of experimental research, screening of new drugs, development of animal models and also in the context of therapy, in particular of human therapy, as explained previously.

Inventors herein provide nucleic acid molecules that down regulate expression of presynaptic cholinergic proteins by RNA interference, in particular nucleic acid molecules producing miRNA, shRNA and/or siRNA molecules, and vectors carrying such molecules, including in particular plasmids and viral vectors.

The inventors herein demonstrate the specificity and efficiency of these nucleic acid molecules and vectors capable of inhibiting in particular ChAT expression in cholinergic neurons of the nervous system. The vectors were shown to be effective in vitro, as well as in vivo in particular in the rat and the mouse (see experimental part of the present application).

The vectors benefit from the technology of ribonucleic acid interference (RNAi), which is described above in great details.

Employing siRNAs in living animals was a challenge, since siRNAs show different effectiveness in different cell types in a manner yet poorly understood: some cells respond well to siRNAs and show a robust knockdown, others show no such knockdown (even despite efficient transfection). However it was a successful approach, which proved to be both safe and very efficient.

Nucleic Acid Molecules Capable of Mediating RNA Interference

Herein described is a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes a cholinergic protein. The cholinergic protein is preferably selected from the choline acetyltransferase (ChAT), the vesicular acetylcholine transporter (VAChT) and the high-affinity choline transporter (CHT1).

Preferred molecules capable of mediating RNA interference advantageously down regulate at least 60%, preferably at least 70%, preferably at least 80%, even more preferably at least 90% or 95%, of the target protein expression (see table 1 in the experimental part).

Preferred siRNA designed to silence a gene encoding ChAT in the rat and the mouse are listed and identified below:

Sense and antisense sequences of the herein called siRNA A:

```
Sense sequence:
5'-CCUGAAGAGCAGUUCAGGAUU-3' is herein identified as SEQ ID NO: 1, Antisense sequence:
5'-UCCUGAACUGCUCUUCAGGUU-3' is herein identified as SEQ ID NO: 2
```

Sense and antisense sequences of the herein called siRNA B:

```
Sense sequence: 5'-GCACUUCCAAGACACCAAUUU-3'
is herein identified as SEQ ID NO: 3

Antisense sequence: 5'-AUUGGUGUCUUGGAAGUGCUU-3'
is herein identified as SEQ ID NO: 4
```

Sense and antisense sequences of the herein called siRNA C:

```
Sense sequence: 5'-CUGGUGUGCUUAGCUACAAUU-3'
is herein identified as SEQ ID NO: 5

Antisense sequence: 5'-UUGUAGCUAAGCACACCAGUU-3'
is herein identified as SEQ ID NO: 6
```

Sense and antisense sequences of the herein called siRNA D:

```
Sense sequence: 5'-GUGAUCUGUUCACUCAGUUUU-3'
is herein identified as SEQ ID NO: 7

Antisense sequence: 5'-AACUGAGUGAACAGAUCACUU-3'
is herein identified as SEQ ID NO: 8
```

Sense and antisense sequences of the herein called siRNA E:

```
Sense sequence: 5'-UAACCGGCAUGGCCAUUGAUU-3'
is herein identified as SEQ ID NO: 9

Antisense sequence: 5'-UCAAUGGCCAUGCCGGUUAUU-3'
is herein identified as SEQ ID NO: 10
```

Sense and antisense sequences of the herein called siRNA F:

```
Sense sequence: 5'-GAGCCACCUGAGAUGUUCAUU-3'
is herein identified as SEQ ID NO: 11

Antisense sequence: 5'-UGAACAUCUCAGGUGGCUCUU-3'
is herein identified as SEQ ID NO: 12
```

Sense and antisense sequences of the herein called siRNA G:

```
Sense sequence: 5'-GAGCGAGCCUUGUUGACAUUU-3'
is herein identified as SEQ ID NO: 13

Antisense sequence: 5'-AUGUCAACAAGGCUCGCUCUU-3'
is herein identified as SEQ ID NO: 14
```

The above described siRNA molecules may be either synthesized or produced by cleavage of corresponding shRNAs by DICER. Such shRNAs can be produced from vectors comprising corresponding nucleic acid sequences. Nucleic acid sequences producing functional shRNAs, from which the active siRNAs identified above are derived, are indicated below. The sequences in bold correspond to the siRNA sequences produced after cleavage of the shRNA by DICER. The $(Z)_n$ sequence represents a loop sequence. A loop of nine nucleotides with the following sequence: TTCAAGAGA (SEQ ID NO: 64), was used by the inventors. Such a loop is however to be considered as an example. The nucleotide nature and number may indeed vary and can be adapted by the man of the art according to known methods.

```
SEQ ID NO 15 (A):
5'-CCTGAAGAGCAGTTCAGGA(Z)ₙTCCTGAACTGCTCTTCAGGTTTT

T-3'

SEQ ID NO 16 (B):
5'-GCACTTCCAAGACACCAAT(Z)ₙATTGGTGTCTTGGAAGTGCTTTT

T-3'

SEQ ID NO 17 (C):
5'-CTGGTGTGCTTAGCTACAA(Z)ₙTTGTAGCTAAGCACACCAGTTTT

T-3'

SEQ ID NO 18 (D):
5'-GTGATCTGTTCACTCAGTT(Z)ₙAACTGAGTGAACAGATCACTTTT

T-3'

SEQ ID NO 19 (E):
5'-TAACCGGCATGGCCATTGA(Z)ₙTCAATGGCCATGCCGGTTATTTT

T-3'

SEQ ID NO 20 (F):
5'-GAGCCACCTGAGATGTTCA(Z)ₙTGAACATCTCAGGTGGCTCTTTT

T-3'

SEQ ID NO 21 (G):
5'-GAGCGAGCCTTGTTGACAT(Z)ₙATGTCAACAAGGCTCGCTCTTTT

T-3'
```

Inventors herein identify the SEQ ID NO:13, 14 and 21 (G) as sequences allowing a particularly efficient inhibition of ChAT expression using RNA interference.

A preferred nucleic acid sequence is a sequence wherein the siRNA is designed to silence the expression of a gene that encodes choline acetyltransferase (ChAT) and the sense and antisense sequences of said siRNA are selected in the group consisting of:

```
5'-GAGCGAGCCUUGUUGACAUUU-3'    (SEQ ID NO: 13)
and

5'-AUGUCAACAAGGCUCGCUCUU-3'    (SEQ ID NO: 14)
[siRNA G];

5'-GCACUUCCAAGACACCAAUUU-3'    (SEQ ID NO: 3)
and

5'-AUUGGUGUCUUGGAAGUGCUU-3'    (SEQ ID NO: 4)
[siRNA B];

5'-CUGGUGUGCUUAGCUACAAUU-3'    (SEQ ID NO: 5)
and

5'-UUGUAGCUAAGCACACCAGUU-3'    (SEQ ID NO: 6)
[siRNA C];

5'-GAGCCACCUGAGAUGUUCAUU-3'    (SEQ ID NO: 11)
and

5'-UGAACAUCUCAGGUGGCUCUU-3'    (SEQ ID NO: 12)
[siRNA F];
``` and any variant thereof comprising at least 18, 19, 20 or 21 consecutive bases in common with one of said sequences.

Inventors herein demonstrate that said shRNA is able to modulate (e.g., down-regulate, inhibit or knock down) at least 95%, preferably at least 98%, even more preferably at least 99% of endogenous ChAT production in cultured cholinergic cells.

Other preferred shRNAs designed to silence the rat and murine genes encoding ChAT may be selected from SEQ ID NO 16 (B), SEQ ID NO 17 (C) and SEQ ID NO 20 (F). The corresponding siRNA are, herein identified as siRNA B (SEQ ID NO: 3 and SEQ ID NO: 4), siRNA C (SEQ ID NO: 5 and SEQ ID NO: 6) and siRNA F (SEQ ID NO: 11 and SEQ ID NO: 12).

Other usable sequences designed to silence the human gene encoding ChAT are listed below:

```
Sense sequence: 5'-GGCUGAAUGACAUGUAUCUUU-3'
is herein identified as SEQ ID NO: 22

Antisense sequence: 5'-AGAUACAUGUCAUUCAGCCUU-3'
is herein identified as SEQ ID NO: 23

Sense sequence: 5'-CUGGUGUACUCAGCUACAAUU-3'
is herein identified as SEQ ID NO: 24

Antisense sequence: 5'-UUGUAGCUGAGUACACCAGUU-3'
is herein identified as SEQ ID NO: 25

Sense sequence: 5'-GCCUCAUUGACAUGAGAGAUU-3'
is herein identified as SEQ ID NO: 26

Antisense sequence: 5'-UCUCUCAUGUCAAUGAGGCUU-3'
is herein identified as SEQ ID NO: 27

Sense sequence: 5'-GAGAUGUUCAUGGAUGAAAUU-3'
is herein identified as SEQ ID NO: 28

Antisense sequence: 5'-UUUAUCCAUGAACAUCUCUU-3'
is herein identified as SEQ ID NO: 29

Sense sequence: 5'-GAGACUUCUUCUAGCAAGUUU-3'
is herein identified as SEQ ID NO: 30

Antisense sequence: 5'- ACUUGCUAGAAGAAGUCUCUU-3'
is herein identified as SEQ ID NO: 31
```

Other usable sequences designed to silence the rat and murine genes encoding CHT1 are listed below:

```
Sense sequence: 5'-GACCAUUCUAGUCAGAAAUUU-3'
is herein identified as SEQ ID NO: 32

Antisense sequence: 5'-AUUUCUGACUAGAAUGGUCUU-3'
is herein identified as SEQ ID NO: 33

Sense sequence: 5'-GGCACCCAUUGGAUAUUCUUU-3'
is herein identified as SEQ ID NO: 34

Antisense sequence: 5'-AGAAUAUCCAAUGGGUGCCUU-3'
is herein identified as SEQ ID NO: 35

Sense sequence: 5'-GCUCUACUCUGUGGCAUAUUU-3'
is herein identified as SEQ ID NO: 36

Antisense sequence: 5'-AUAUGCCACAGAGUAGAGCUU-3'
is herein identified as SEQ ID NO: 37

Sense sequence: 5'-CCUGACAAGAAUGGUAUAUUU-3'
is herein identified as SEQ ID NO: 38

Antisense sequence: 5'-AUAUACCAUUCUUGUCAGGUU-3'
is herein identified as SEQ ID NO: 39
```

Other usable sequences designed to silence the human gene encoding CHT1 are listed below:

```
Sense sequence: 5'-GGCCGAGUAUUGGUUUAUUU-3'
is herein identified as SEQ ID NO: 40

Antisense sequence: 5'-AUAAACCAAUAUCUCGGCCUU-3'
is herein identified as SEQ ID NO: 41

Sense sequence: 5'-GGCCUUCCUUGAUGUUGAUUU-3'
is herein identified as SEQ ID NO: 42

Antisense sequence: 5'-AUCAACAUCAAGGAAGGCCUU-3'
is herein identified as SEQ ID NO: 43

Sense sequence: 5'-GGCACCAAUGGAUAUUCUUU-3'
is herein identified as SEQ ID NO: 44

Antisense sequence: 5'-AGAAUAUCCAAUUGGUGCCUU-3'
is herein identified as SEQ ID NO: 45

Sense sequence: 5'-CUGCUGUGCAUGCCAAAUAUU-3'
is herein identified as SEQ ID NO: 46

Antisense sequence: 5'-UAUUUGGCAUGCACAGCAGUU-3'
is herein identified as SEQ ID NO: 47
```

Other usable sequences designed to silence the rat and murine genes encoding VAChT are listed below:

```
Sense sequence: 5'-GGCCUUUCAUUGAUCGCAUUU-3'
is herein identified as SEQ ID NO: 48

Antisense sequence: 5'-AUGCGAUCAAUGAAAGGCCUU-3'
is herein identified as SEQ ID NO: 49

Sense sequence: 5'-CACUGUUACUGGACAACAUUU-3'
is herein identified as SEQ ID NO : 50

Antisense sequence: 5'-AUGUUGUCCAGUAACAGUGUU-3'
is herein identified as SEQ ID NO: 51

Sense sequence: 5'-GCGAUGUGUUGCUUGAUGAUU-3'
is herein identified as SEQ ID NO: 52

Antisense sequence: 5'-UCAUCAAGCAACACAUCGCUU-3'
is herein identified as SEQ ID NO: 53
```

-continued

```
Sense sequence: 5'-CUGGACAACAUGUUGUACAUU-3'
is herein identified as SEQ ID NO: 54

Antisense sequence: 5'-UGUACAACAUGUUGUCCAGUU-3'
is herein identified as SEQ ID NO : 55
```

Other usable sequences designed to silence the human gene encoding VAChT are listed below:

```
Sense sequence: 5'-CGCUGUUACUGGACAACAUUU-3'
is herein identified as SEQ ID NO: 56

Antisense sequence: 5'-AUGUUGUCCAGUAACAGCGUU-3'
is herein identified as SEQ ID NO: 57

Sense sequence: 5'-GCCUUCAUUAGCUUCGGAAUU-3'
is herein identified as SEQ ID NO: 58

Antisense sequence: 5'-UUCCGAAGCUAAUGAAGGCUU-3'
is herein identified as SEQ ID NO: 59

Sense sequence: 5'-GAGGACGACUACAACUACUUU-3'
is herein identified as SEQ ID NO: 60

Antisense sequence: 5'-AGUAGUUGUAGUCGUCCUCUU-3'
is herein identified as SEQ ID NO: 61

Sense sequence: 5'-GACGACUACAACUACUACUUU-3'
is herein identified as SEQ ID NO: 62

Antisense sequence: 5'-AGUAGUAGUUGUAGUCGUCUU-3'
is herein identified as SEQ ID NO: 63
```

Inventors further demonstrate that the above described nucleic acid molecule, capable of mediating RNA interference, can be safely, efficiently and durably expressed in target cells by using appropriate expression vectors herein described.

Vectors, in particular lentiviral vectors, expressing the corresponding RNA are herein provided.

The present disclosure encompasses any viral vector comprising a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes a cholinergic protein as defined previously, wherein the virus vector is preferably selected from the group consisting of a lentivirus, an adenovirus, an adenovirus associated virus, and an herpes simplex virus.

Lentiviral Vectors

An appropriate expression vector is a non replicative lentivirus comprising a lentiviral genome comprising a nucleic acid sequence producing at least one functional micro RNA (miRNA), at least one functional short-hairpin RNA (shRNA) and/or at least one functional small interfering RNA (siRNA), said siRNA being preferably derived from said shRNA, said miRNA, shRNA and siRNA being designed to silence the expression of a gene that encodes a presynaptic cholinergic protein, said lentivirus being pseudotyped for the selective transfer of the lentiviral genome into cells of the nervous system (e.g., central or peripheral nervous system), preferably into neuronal cells, even more preferably into cholinergic neurones, or into non neuronal cells producing acetylcholine.

In a particular embodiment, the non replicative lentivirus of the invention, comprises a lentiviral genome as previously described further comprising a second nucleic acid sequence producing at least one functional miRNA, at least one functional shRNA and/or at least one functional siRNA, preferably derived from said shRNA, said miRNA, shRNA and siRNA being designed to silence the expression of a gene encoding a different protein of the cholinergic pathway, preferably a protein selected from the group consisting of ChAT, CHT1 and VAChT.

Lentiviruses are complex retroviruses capable of transducing cells which are not mitotically active, such as cells of the nervous system, in particular certain cell subpopulations of the central nervous system such as neuronal cells. These viruses include in particular Human Immunodeficiency Virus type 1 (HIV-1), Human Immunodeficiency Virus type 2 (HIV-2), Simian Immunodeficiency Virus (SIV), Feline Immunodeficiency Virus (FIV), Equine Infectious Anaemia Virus (EIAV), Bovine Immunodeficiency Virus (BIV), Visna Virus of sheep (VISNA) and Caprine Arthritis-Encephalitis Virus (CAEV). A preferred lentivirus according to the present invention is selected in the above mentioned list of viruses.

Like other retroviruses, lentiviruses have gag, pol and env genes flanked by two LTR (Long Terminal Repeat) sequences. Each of these genes encodes many proteins which are initially expressed in the form of a single precursor polypeptide. The gag gene encodes the internal structural proteins (capsids and nucleocapsids). The poi gene encodes the reverse transcriptase, the integrase and the protease. The env gene encodes the viral envelope glycoprotein and also contains a cis-acting RRE (Rev Responsive Element) responsible for exporting the viral RNA out of the nucleus. The 5' and 3' LTR sequences serve to promote the transcription and the polyadenylation of the viral RNAs. The LTR contains all the other cis-acting sequences necessary for viral replication. Sequences necessary for the reverse transcription of the genome (tRNA primer binding site) and for encapsidation of the viral RNA into particles (site $\Psi$) are adjacent to the 5' LTR. If the sequences necessary for encapsidation (or for packaging of the retroviral RNA into infectious virions) are absent from the viral genome, the genomic RNA will not be actively encapsidated.

The construction of lentiviral vectors for gene transfer applications has been described, for example, in U.S. Pat. No. 5,665,577, EP 386 882, U.S. Pat. Nos. 5,981,276 and 6,013,516 or else in patent application WO 99/58701.

The vectors used in the present invention are non replicative, in other words they comprise a defective lentiviral genome, i.e., a genome in which at least one of the gag, pol and env genes has been inactivated or deleted. These vector genomes are encapsidated in a protein particle composed of the structural lentiviral proteins and in particular of an envelope glycoprotein, preferably of a heterologous envelope glycoprotein.

The recombinant lentiviruses according to the invention are thus genetically modified in such a way that certain genes constituting the native infectious virus are eliminated and replaced with a nucleic acid sequence of interest to be introduced into the target cells. After adsorption of the virus on the cell membrane, said virus injects its nucleic acid into the cell and, after reverse transcription, said nucleic acid can integrate into the genome of the host cell. The genetic material thus transferred is then transcribed and possibly translated into proteins inside the host cell. When the lentiviral vector is a non integrative lentiviral vector, the genetic material transferred in host cells is present in episomal forms.

A preferred non replicative lentivirus herein described is a lentivirus deprived of any lentiviral coding sequence. It is also deleted of the enhancer region of the U3 region of the LTR3'. Particularly preferred lentiviral vectors are pseudotyped vectors that allow transduction of a cell population of the nervous system, in particular of the central nervous system. The term "pseudotyping" denotes a recombinant virus comprising an envelope different from the wild-type envelope. In the context of the present invention, the vectors express an envelop protein which direct the vector to various cells, including the cells of the central nervous system. Also herein described is the targeting of a particular cell population of the nervous system, in particular of the central nervous system. Preferred targeted cells are cholinergic neurons of well defined areas such as the medial septum of the brain, or other herein cited brain areas, of an animal. Other cells which may be targeted are non neuronal cells producing acetylcholine.

A preferred envelope glycoprotein is an envelope glycoprotein of a Rhabdovirus, in particular a vesiculovirus envelope glycoprotein such as the envelope glycoprotein of the vesicular stomatitis virus (VSV). This envelope exhibits advantageous characteristics, such as resistance to ultracentrifugation and a very broad tropism. Unlike other envelopes, such as those of the conventional retroviruses (amphotropic and ecotropic MLV retroviruses or HIV gp120, but also many others), the VSV glycoprotein is not labile after ultracentrifugation. This makes it possible to concentrate the viral supernatants and to obtain high infectious titres. Moreover, this envelope confers on the virions a very broad tropism, in particular in vitro, allowing the infection of a very large number of cell types, including cells of the central nervous system, in particular neuronal cells. VSV-G is the VSV envelop glycoprotein.

Preferred vectors allow targeting of neurons, preferably neurons of the cholinergic type. These pseudotyped viral vectors are useful for the transfer and the expression in vitro, ex vivo and in vivo of nucleic acid sequences of interest preferentially within neurons.

The term "preferentially" should be understood to mean that the lentiviruses according to the invention target essentially neurons but are, nevertheless, capable of transfecting other cell types. Other cell subpopulations which may be targeted by vectors of the invention are, for example, blood, urinary bladder, placental, ganglionic or muscular cells.

Other preferred envelopes are lyssavirus envelopes, in particular a virus envelop of the rabies virus serogroup selected from the group consisting of Rabies (RAB); Duvenhague (DUV), European Bat type 1 (EB-1), European Bat type 2 (EB-2), Kotonkan (KOT), Lagos Bat (LB), Mokola (MOK), Obodhiang (OBD) and Rochambeau (RBU), or any chimeric composition of these envelopes. In a preferred embodiment, inventors use lentiviral vectors, for example of the HIV type, pseudotyped with an envelope of the PV (rabies virus) or MOK (Mokola virus) type.

In a particular embodiment, the lentivirus comprises a lentiviral genome (lentiviral RNA genome) comprising, between wild type LTR5' and LTR3' sequences or modified (att mutants) LTR5' and/or LTR3' sequences, a lentiviral Psi ($\psi$) encapsidation sequence, at least one nucleic acid sequence producing at least one functional miRNA, at least one functional shRNA, at least one functional siRNA preferably derived from a relevant shRNA or miRNA, and/or a promoter, and optionally a sequence enhancing the nuclear import of the retrotranscribed viral DNA (viral genome) such as the cppT-CTS, a transcriptional regulation element and/or a post-transcriptional regulatory element. A sequence regulating, preferably enhancing, nuclear export of the RNA viral genome (during the production of the vector) may advantageously be added. In addition, during the production, a mutated integrase gene may be used (in the transcomplementary plasmid) in order to obtain a non integrative lentiviral vector.

The above mentioned promoter can be a viral or a cellular promoter.

A preferred cellular promoter usable, in the context of the present invention, to express a shRNA, may be a RNA polymerase III promoter selected from the group consisting of H1, U6, and 7SK.

A preferred viral promoter usable, in the context of the present invention, to express a miRNA targeting a presynaptic cholinergic protein such as ChAT, may be a polymerase II promoter selected from the group consisting of CMV, TK and RSV LTR.

A preferred cellular promoter usable, in the context of the present invention, to express a miRNA targeting a presynaptic cholinergic protein such as ChAT, may be a polymerase II promoter selected from the group consisting of PGK, Rho, EF1$\alpha$, Thy1, ChAT, VAChT, CHT1, neuron-specific enolase (NSE), Nestin and S100$\beta$.

In a particular embodiment, the promoter may be a chimeric promoter composed of a minimal polymerase II or polymerase III promoter under the control of transcriptional regulatory elements such as enhancer [for example the neuron-restrictive silencer element (NRSE)] or silencer sequences. An example of chimeric promoter is the cytomegalovirus immediate early enhancer-chicken beta-actin hybrid (CAG) promoter (Okabe et al., 1997). In a particular embodiment, the promoter is a transactivator induced promoter as further explained below, comprising at least one transactivator binding sequence, preferably a plurality of transactivator binding sequences, operatively linked to the nucleic acid sequence producing at least one functional micro RNA (miRNA), at least one functional short-hairpin RNA (shRNA) and/or at least one functional small interfering RNA (siRNA).

A particularly preferred sequence enhancing the nuclear import of the retrotranscribed viral DNA (viral genome) is the lentiviral cPPT CTS (flap) sequence from HIV-1. Other sequences, usable in the context of the present invention, enhancing DNA nuclear import are lentiviral cPPT CTS sequences from (HIV-2, SIV, FIV, EIAV, BIV,VISNA and CAEV). A particularly preferred sequence enhancing the RNA nuclear export, advantageous during the production, is a sequence comprising the HIV-1 REV response element (RRE) sequence. Another sequence, usable in the context of the present invention, which enhances the RNA nuclear export, is the CTE sequence (Oh et al, 2007). Preferred post-transcriptional regulation elements may be selected from Woodchuck hepatitis virus responsive element (WPRE), APP UTR5' region and TAU UTR3'. Another preferred regulation element is an insulator sequence selected from the group consisting of, for example, MAR, SAR, S/MAR, scs and scs' sequences.

A preferred lentivirus is non integrative (EP 1761635). Such a lentivirus comprises a mutated integrase in order to limit the risk of genotoxicity. Preferably the integrase mutation is a class I mutation (Engelman, 1999). Preferably the integrase comprises a mutation in at least one of its basic region and/or catalytic region (Philippe et al., 2006). The lentivirus integration can also be silenced by mutating the att sequence in one or both LTRs, by mutating the CA motif of the att sequence (Nightinghale et al., 2006)

The lentiviral vectors according to the invention can be prepared in various ways, notably by transient transfection(s) into producer cells (or using stable producer cell lines) and/or by means of helper viruses.

The method according to the invention comprises the transfection of a combination of a minimum of two plasmids. According to a particularly preferred embodiment, the method according to the invention comprises the transfection of a combination of a minimum of three plasmids in order to produce a recombinant virion or a recombinant retrovirus.

A first plasmid provides the lentiviral vector genome comprising the cis-acting viral sequences necessary for the correct functioning of the viral cycle. Such sequences include preferably one or more lentiviral LTRs, a Psi (ψ) packaging sequence, reverse transcription signals, a promoter and/or an enhancer and/or polyadenylation sequences. In this vector, the LTRs can also be modified so as to improve the expression of the transgene or the safety of the vector. Thus, it is possible to modify, for example, the sequence of the 3' LTR by eliminating the U3 region [modified sequence herein identified as LTR(ΔU3)] (see WO 99/31251). One can also introduce the transgene cassette (promoter+transgene) in the vector genome between the LTRs, or in place of the U3 region of the LTR 3'.

According to a particular embodiment of the invention, it is a vector plasmid comprising a recombinant lentiviral genome of sequence LTR-psi-Promoter-transgene-LTR which allows expression of the vector RNA which will be encapsidated in the virions.

A preferred vector plasmid comprises a recombinant lentiviral genome of sequence LTR-psi-flap-Promoter-transgene-LTR, wherein flap designates the sequence cPPT CTS enhancing the DNA nuclear import.

Another preferred vector plasmid comprises a recombinant lentiviral genome of sequence LTR-psi-flap-Promoter-transgene-LTR, wherein flap designates the sequence cPPT CTS which improves the transduction of non dividing cells, and in particular which enhances the DNA nuclear import. A WPRE (Woodchuck hepatitis virus responsive element) is a transcription regulation element which may be used to enhance the transgene expression level. The order of flap, promoter and transgene elements in the plasmid sequence can be modified, for example promoter-flap-transgene or promoter-transgene-flap.

In the present invention, the transgene or nucleic acid of interest produces at least one functional nucleic acid molecule capable of mediating RNA interference, preferably at least one functional miRNA, at least one functional short-hairpin RNA (shRNA), and/or at least one functional siRNA derived from said shRNA, said nucleic acid molecule being designed to silence the expression of at least one target gene, in particular a gene that encodes a presynaptic cholinergic protein such as ChAT.

The transgene is typically placed under the control of a transcriptional promoter. A promoter that is particularly useful in the context of the present invention has a transcription machinery that is compatible with mammalian genes, can be compatible with expression of genes from a wide variety of species, preferably has a high basal transcription rate, recognizes termination sites with a high level of accuracy. A preferred promoter will preferably be sufficient to direct the transcription of a distally located sequence, which is a sequence linked to the 3' end of the promoter sequence in a cell.

Since long poly A tails compromise the silencing effect of shRNAs, their expression is appropriately driven by RNA polymerase III which recognizes a run of 5T residues as a stop signal and does not therefore require a poly A sequence to terminate transcription.

Suitable promoters include, for example, RNA polymerase (pol) III promoters including, but not limited to, the (human and murine) H1 promoters, the (human and murine) U6 promoters, and the (human and murine) 7SK promoters. In addition, a hybrid promoter also can be prepared that contains elements derived from, for example, distinct types of RNA polymerase (pol) III promoters. Modified promoters that contain sequence elements derived from two or more naturally occurring promoter sequences can be combined by the skilled person to effect transcription under a desired set of conditions or in a specific context. For example, the human and murine U6 RNA polymerase (pol) III and H1 RNA pol III promoters are well characterized and useful for practicing the invention. One skilled in the art will be able to select and/or modify the promoter that is most effective for the desired application and cell type so as to optimize modulation of the expression of one or more genes. The promoter sequence can be one that does not occur in nature, so long as it functions in a eukaryotic cell, preferably a mammalian cell.

Expression of the transgene or nucleic acid of interest, here at least one functional miRNA, shRNA or siRNA derived from said shRNA or miRNA, may be externally controlled by treating the cell with a modulating factor, such as tetracycline, rapamycin or an analog thereof. Analogs of tetracycline are for example chlortetracycline, oxytetracycline, demethylchloro-tetracycline, methacycline, doxycycline and minocycline. Analogs of rapamycin are for example CCI-779, AP21967, AP23573.

Conditional suppression of genes may indeed be important for therapeutic applications by allowing time and/or dosage control of the treatment or by permitting to terminate treatments at the onset of unwanted side effects.

Reversible gene silencing may be implemented using a transactivator induced promoter together with said transactivator. Such a transactivator induced promoter comprises control elements for the enhancement or repression of transcription of the transgene or nucleic acid of interest producing miRNA, shRNA and/or siRNA. Control elements include, without limitation, operators, enhancers and promoters. A transactivator inducible promoter, in the context of the present invention, is transcriptionally active when bound to a transactivator, which in turn is activated under a specific set of conditions, for example, in the presence or in the absence of a particular combination of chemical signals, preferably by a modulating factor selected for example from the previous list.

The transactivator induced promoter may be any promoter herein mentioned which has been modified to incorporate at least one transactivator binding sequence operatively linked to the nucleic acid sequence producing at least one functional micro RNA (miRNA), at least one functional short-hairpin RNA (shRNA) and/or at least one functional small interfering RNA (siRNA), preferably several transactivator binding sequences, such as several tet-operon sequences, for example 7 tet-operon sequences, preferably in tandem. Such sequences can for example replace the functional recognition sites for Staf and Oct-1 in the distal sequence element (DSE) of a polymerase III promoter, preferably of the human U6, H1 or 7SK polymerase III promoter.

Advantageously, the transactivator induced promoter comprises a plurality of transactivator binding sequences operatively linked to the nucleic acid sequence producing miRNA, shRNA and/or siRNA.

The transactivator may be provided by a nucleic acid sequence, in the same expression vector or in a different expression vector, comprising a modulating factor-dependent promoter operatively linked to a sequence encoding the transactivator. The term "different expression vector" is intended to include any vehicle for delivery of a nucleic acid, for example, a virus, plasmid, cosmid or transposon. Suitable promoters for use in said nucleic acid sequence include, for example, constitutive, regulated, tissue-specific or ubiquitous promoters, which may be of cellular, viral or synthetic origin, such as CMV, RSV, PGK, EF1α, NSE, synapsin, β-actin, ChAT, VAChT, CHT1, Thy1.

A preferred transactivator for a polymerase III promoter according to the present invention is the tetR-KRAB (tetracycline repressor-Krüppel-associated box) transactivator (for review see Wiznerowicz et al., 2006).

Another preferred transactivator for a polymerase III promoter according to the present invention is the rtTA-Oct.2 transactivator composed of the DNA binding domain of rtTA2-M2 and of the Oct-2$^Q$(Q→A) activation domain.

Another preferred transactivator for a polymerase III promoter according to the present invention is the rtTA-Oct.3 transactivator composed of the DNA binding domain of the Tet-repressor protein (E. coli) and of the Oct-2$^Q$(Q→A) activation domain.

Both latter are described in patent application WO 2007/004062.

A preferred transactivator for a polymerase II promoter according to the present invention is the tetR-KRAB transactivator (for review see Wiznerowicz et al., 2006).

Another preferred transactivator for a polymerase II promoter according to the present invention is the tetracycline inducible tetR-VP16 transactivator (for review see Wiznerowicz et al., 2006).

Another preferred transactivator for a polymerase II promoter according to the present invention is a rapamycin inducible transactivator (for review see Clackson, 1997).

As used herein, the term "operatively linked" means that the elements are connected in a manner such that each element can serve its intended function and the elements, together can serve their intended function. In reference to elements that regulate gene expression, "operatively linked" means that a first regulatory element or coding sequence in a nucleotide sequence is located and oriented in relation to a second regulatory element or coding sequence in the same nucleic acid so that the first regulatory element or coding sequence operates in its intended manner in relation with the second regulatory element or coding sequence.

When the lentivirus comprises a transactivator induced promoter, said lentivirus may further advantageously comprise a WPRE which is able to enhance the expression of the transactivator.

A second plasmid, for trans-complementation, provides a nucleic acid encoding the protein products of the gag and pol lentiviral genes. These proteins are derived from a lentivirus and preferably originate from HIV, in particular HIV-1. The second plasmid is devoid of encapsidation sequence, of sequence encoding an envelope and, advantageously, is also devoid of lentiviral LTRs. As a result, the sequences encoding gag and pol proteins are advantageously placed under control of a heterologous promoter, for example a viral, cellular, etc. promoter, which may be constitutive or regulated, weak or strong. It is preferably a trans-complementing plasmid comprising a sequence CMV-Δpsi-gag-pol-Δenv-PolyA. This plasmid allows the expression of all the proteins necessary for the formation of empty virions, except the envelope glycoproteins. It is understood that the gag and pol genes may also be carried by different plasmids.

A third plasmid provides a nucleic acid which allows the production of the chosen envelope (env) glycoprotein. This envelope may be chosen from the envelopes mentioned above, in particular an envelope of a rhabdovirus. This vector is preferentially devoid of all lentiviral sequences.

Advantageously, the three vectors used do not contain any homologous sequence sufficient to allow a recombination. The nucleic acids encoding gag, pol and env may advantageously be cDNAs prepared according to conventional techniques, from sequences of the viral genes available in the prior art and on databases.

For the production of the non replicative lentiviruses, the vectors described above are introduced into competent cells and the viruses produced are harvested. The cells used may be any competent cell, preferably mammalian cell, for example animal or human cell, which is non pathogenic. Mention may, for example, be made of 293 cells, embryonic cells, fibroblasts, muscle cells, etc.

A preferred method for preparing a non replicative recombinant lentivirus, according to the invention, comprises transfecting a population of competent cells with a combination of vectors (two vectors, three vectors or more than three vectors) as described above, and recovering the viruses thus produced.

A particularly advantageous method for producing lentiviruses capable of reducing, inhibiting or silencing in vivo the expression of a gene that encodes a presynaptic cholinergic protein, in particular in human neurons, comprises transfection of competent cells with:

a vector plasmid comprising a sequence, as described previously, such as LTR-psi-Promoter-transgene-LTR(ΔU3), a trans-complementing plasmid comprising a sequence CMV-Δpsi-gag-pol-Δenv-PolyA, and an envelope plasmid comprising a sequence CMV-env-PolyA, the envelope being preferably an envelope of the rhabdovirus family.

The lentiviruses of the invention may also be prepared, as explained previously, from an encapsidation cell line producing one or more gag, pol and env proteins.

A recombinant cell comprising a nucleic acid sequence or vector virus according to the present invention is further herein disclosed as well as an animal (for example an animal model), in particular a non-human animal such as a rodent, in particular a rat or a mouse, comprising such a nucleic acid, vector or recombinant cell.

Uses

The present disclosure provides a method for modulating (e.g. decreasing, suppressing or silencing) the expression of a gene that encodes a cholinergic protein, such as ChAT, in a cell or an animal, the method comprising administering to said cell or animal a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes said cholinergic protein, a viral vector as herein described encoding such a nucleic acid sequence, or a composition comprising such a nucleic acid sequence or viral vector.

A particular method for modulating the expression of a gene that encodes a cholinergic protein comprises the steps of administering to the cell or animal, a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes said cholinergic protein, a viral vector encoding such a nucleic acid sequence, or a composition comprising such a nucleic acid sequence or viral vector, and placing the cell or animal under conditions wherein the miRNA, shRNA and/or siRNA is/are expressed in an amount sufficient to cause a detectable modulation, preferably the decrease or even more preferably the silencing, of the gene expression.

Such a detectable modulation may be determined using methods know by the man of the art, usable to estimate the expression of a mRNA, such as PCR and Northern Blot, or a protein, such as immunohistochemical experiments, western blots or the measure of the cholinergic protein activity or function.

The step of introducing into the cell or animal a viral vector or a composition according to the present invention results in expression of the nucleotide sequence encoding the at least one functional miRNA, at least one functional short-hairpin RNA (shRNA) and/or at least one functional siRNA preferably for longer than three weeks, preferably longer than a month.

The viral vectors according to the invention, in particular the lentiviruses, may be used for preparing a composition intended for gene transfer into neurons in vivo or ex vivo, in particular local gene transfer into neurons of a well delimited cholinergic area of the central nervous system such as the medial septum, the basal nucleus of Meynert, the laterodorsal and pedunculopontine tegmental nuclei, the striatum or motoneurons.

The nucleic acids and viral vectors according to the invention may further be used for preparing a composition intended for gene transfer into cells of the peripheral nervous system, for example in cholinergic neurons of the intestine, or into non neuronal cells, in particular cells which produce acetylcholine such as blood or placental cells.

Also herein provided is a method for producing an animal model wherein a target gene encoding a particular cholinergic protein is modulated, preferably repressed or silenced, in at least one particular nucleus of the central nervous system of said animal. Such a method may advantageously comprise the administration to said animal of a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes said cholinergic protein, a viral vector as herein described encoding such a nucleic acid sequence, or a composition as herein described comprising such a nucleic acid sequence or viral vector.

The function of a particular cholinergic nucleus of the central nervous system of such an animal model can thus be specifically identified or studied.

The present disclosure also encompasses an animal model of a disease wherein cholinergic neurons are impaired in at least one specific region (as herein mentioned) of the nervous system of said animal model.

The nervous system disorder may be a brain or spinal cord trauma or a stroke.

The disorder may also be any condition involving the cholinergic system or affecting its pathways, in particular a disorder associated with a deregulated acetylcholine expression, preferably a decreased acetylcholine expression, for example a brain or spinal cord trauma, a stroke, or a neurodegenerative disease, including, but not limited to Alzheimer's disease, motoneuron diseases, Amyotrophic lateral sclerosis (ALS).

The herein described products (nucleic acids, viral vectors, compositions, kits, etc.) and methods are advantageously usable to identify molecular networks regulated by cholinergic neurotransmission.

The nucleic acids and viral vectors according to the invention may further be used for preparing a pharmaceutical composition intended to prevent or treat a nervous system disorder, in particular a central nervous system (CNS) disorder, or alleviate symptoms thereof in an animal subject, preferably a mammal, in particular a human.

In other words, the nucleic acids, viral vectors and compositions (cholinergic antagonists) according to the invention may be used to prevent or treat a nervous system disorder or alleviate the symptoms thereof in an animal.

Cholinergic neurons are indeed involved, as explained previously, in numerous brain circuits and thus play a role in the regulation of other neuronal systems and indirectly in the regulation of the functions governed by the neurons they innervate. For example, cholinergic neurons of the brainstem send their axonal projections to dopaminergic structures: the ventral tegmental area, which is considered as the principal brain region involved in the physiological activity of multiple drugs including nicotine, and the substantia nigra, which is affected in Parkinson's disease. Decreasing or silencing acetylcholine synthesis specifically in such (a) particular brain area(s) by using one of the herein described cholinergic antagonists, selected from a nucleic acid, a viral vector and a composition according to the present invention may thus be a strategy to prevent or treat a brain disease or disorder.

In addition, accidental overdoses with various drugs or pharmaceuticals and contamination by toxins can also be responsible for the relative over-activity of the cholinergic system and may be treated with a cholinergic antagonist of the present invention.

Also provided is thus a method of preventing or treating a nervous system (NS) disorder, in particular a central nervous system (CNS) disorder, or alleviating the symptoms thereof in a subject, in particular a mammal, preferably a human, wherein the method comprises administering to said subject a pharmaceutical composition comprising a cholinergic antagonist as herein described, and a pharmaceutically acceptable carrier or excipient.

An example of a preferred cholinergic antagonist is a non replicative lentivirus comprising a lentiviral genome comprising a nucleic acid sequence producing at least one functional miRNA, at least one functional shRNA, and/or at least one functional siRNA, preferably derived from said miRNA or shRNA, said miRNA, shRNA and siRNA being designed to silence the expression of a gene that encodes a cholinergic protein, said lentivirus being preferably pseudotyped for the selective transfer of the lentiviral genome into cholinergic neurons or into non neuronal cells which synthetize acetylcholine.

Another subject of the invention lies in the combined use of several identical or different viruses, in particular lentiviruses, as herein described, for the purpose of transferring and expressing several identical or different miRNAs, shRNAs and/or siRNA in the cells of the nervous system, in particular in neuronal cells, preferably in cholinergic neurons. The combined use may comprise sequential administrations of the various viruses, or a simultaneous administration.

The lentiviruses of the invention may further allow the transport and the expression, within nerve cells, of at least one nucleic acid encoding for example a compound selected from a growth factor such as FGF, a trophic factor such as GDNF, BDNF, NGF, NT-3, a cytokine, a colony stimulating factor, an anticancer agent, a toxin, an enzyme, a neurotransmitter or a precursor thereof, a component of the extracellular matrix (ECM) such as N-CAM, PAS-NCAM, laminin, fibronectin, N-cadherin, a growth associated protein such as GAP-43, CAP-23 etc., enhancing the activity of the at least one functional nucleic acid molecule capable of mediating RNA interference also produced, and/or enhancing the prophylactic or therapeutic effect thereof.

The viral vectors, in particular the lentivirus vectors, may be purified and conditioned in any suitable composition, solution or buffer, comprising biocompatible or pharmaceutically acceptable excipient, vehicle or carrier, such as a saline, isotonic, buffered solution such as Mannitol 20%, optionally combined with stabilizing agents such as isogenic albumin or any other stabilizing protein, glycerol, etc., and also adjuvants such as polybrene or DEAE dextrans, etc.

The doses of vector may be adjusted by the skilled person depending on the route of administration, the targeted tissue, vector, compound, etc.

The composition comprising a lentivirus as herein described is advantageously administered at a rate of about 0.01 to $10^5$ ng of P24 HIV-1 capsidic protein (or the corresponding equivalent for other viruses), preferably between about 5 to 5000 ng of capsidic protein P24.

Various protocols may be used for the administration, such as simultaneous or sequential administration, single or repeated administration, etc., which may be adjusted by the skilled person.

A lentiviral vector can be used that provides for transient expression of siRNA molecules in the case of non integrative lentiviral vectors. Such vectors can be repeatedly administered as necessary.

The herein described compositions, in particular the pharmaceutical compositions, containing a nucleic acid or viral vectors according to the invention, may be administered to a subject, by intracerebral, intraspinal, intrathecal, systemic, intravenous, intra-arterial or intramuscular injection. Preferred modes of injection are intracerebral injection, intraspinal injection and intrathecal injection.

The injection site may depend on the particular tropism of the selected pseudotyped viral vector, in particular for nervous cells such as neurons of the cholinergic type. In the particular example of a pseudotyped lentiviral vector as herein described, the administration may be performed by intracerebral, intraspinal (preferably directly in the medullar parenchyma), intravenous or intra-arterial injection.

Another preferred mode of administration is the muscular injection of vectors which can be retrogradely transported. Such vectors may be selected in the group consisting of adenoviruses, herpes simplex viruses, a particular serotype of adenovirus associated virus (AAV serotype 8, Stieger et al., 2008), a particular lentivirus serotype (see the lentivirus serotype described in Azzouz & Mazarakis, 2004; Mentis et al., 2006).

Non viral siRNA delivery can also be performed either by injecting siRNA molecules or by injecting a plasmid DNA engineered or designed to express miRNA, shRNA or siRNA.

The previously described siRNA molecules or plasmid may be complexed with polyethylenimine or encapsulated into liposomes or receptor-specific pegylated immunoliposomes (PILS). As PILS are able to cross the blood-brain barrier, this last strategy allows, through intravenous injection, the targeting of particular sites of the central nervous system (Pardridge, 2004).

The identification, by a high throughput screening strategy, of new agonists/antagonists of targets selected upon a biologic hypothesis does not always allow to reach a high level of specificity and thus may lead to unwanted side effects that limit their therapeutical use. Concerning the cholinergic system, the specificity of an antagonist widely used in animal models has been recently reconsidered (McCann et al., 2006). One major advantage of the nucleic acid herein described is their high specificity towards the cholinergic neurotransmission.

The disclosure thus further herein provides a method of screening a compound, in vivo in an animal model or ex vivo in cultured animal cells, preferably cultured human cells, comprising the identification or selection of a compound allowing or enhancing the synthesis of acetylcholine or of a compound compensating an acetylcholine deficit by acting either on the cholinergic neurons themselves or on the target cells of said cholinergic neurons.

In a particular embodiment, the present invention also relates to a method as described previously, wherein said method comprises two steps consisting in contacting an animal or a cell with (i) a nucleic acid, a virus, in particular lentivirus, according to the present invention, or a composition comprising such a nucleic acid or virus, and (ii) with a modulating factor such as tetracycline, as previously described, and wherein said two steps may be inverted.

The target gene expression repression can be reversed upon withdrawal of the modulating factor or upon interruption of the modulating factor treatment or on the contrary upon administration, adjunction or application of a modulating factor, depending, as explained previously, on the transactivator used. Such a method can be realized in a dose- and time-dependent manner.

In another aspect, the present disclosure provides a kit comprising any one of the herein-described nucleic acids, viruses, in particular lentiviruses, or compositions. Generally, the kit also comprises one or more containers filled with one or more of the ingredients of the pharmaceutical compositions of the invention. Associated with such container(s) can be and a leaflet providing guidelines or a notice comprising instructions for using the corresponding product.

Typically, the kit is a kit for expressing a nucleic acid designed to silence the expression of a gene encoding a cholinergic protein, in particular the choline acetyltransferase (ChAT), comprising a nucleic acid sequence producing at least one functional micro RNA (miRNA), at least one functional short-hairpin RNA (shRNA) and/or at least one functional small interfering RNA (siRNA), said miRNA, shRNA and siRNA being designed to silence the expression of a gene that encodes said cholinergic protein, and a leaflet or notice comprising instructions for using the nucleic acid sequence.

A particular kit comprises at least one lentivirus according to the present invention, in particular a non replicative lentivirus, preferably pseudotyped for the selective transfer of the lentiviral genome into cells of the nervous system, comprising a lentiviral genome comprising a nucleic acid sequence producing at least one functional miRNA, at least one functional shRNA and/or at least one functional siRNA, said miRNA, shRNA and siRNA being designed to silence the expression of a gene that encodes a cholinergic protein such as the choline acetyltransferase (ChAT), and a leaflet or notice comprising instructions for using the lentivirus.

Also provided is a cloning kit comprising:
a) a vector plasmid comprising a sequence, as described previously, such as LTR-psi-Promoter-transgene-LTR($\Delta$U3),
b) a trans-complementing plasmid comprising a sequence CMV-$\Delta$psi-gag-pol-$\Delta$env-PolyA,
c) an envelope plasmid comprising a sequence CMV-env-PolyA, the envelope glycoprotein being preferably an envelope glycoprotein of the rhabdovirus virus family, and optionally
d) a leaflet providing guidelines.

Further aspects and advantages of this invention are disclosed in the following experimental section, which should be regarded as illustrative and not limiting the scope of this application in any way.

EXPERIMENTAL PART

The functional role of cholinergic neurons has been analyzed mainly by classical lesion protocols which are not specific for these neurons, or by immunolesion with 192-IgG-Saporin, which selectively destroys basal forebrain cholinergic neurons. Constitutive knockout of the ChAT gene in the mouse is lethal at birth and thus cannot be used to investigate cholinergic function in the adult (Brandon et al., 2003; Misgeld et al., 2002).

Inventors herein report the development of a RNAi approach to generate a loss-of-function phenotype specific to cholinergic neurons in an animal. RNAi was designed to specifically suppress ChAT expression and thus inhibit acetylcholine synthesis and cholinergic neurotransmission both in cultured cells and in vivo in defined brain areas without eliminating the cholinergic neurons.

Inventors first identified one shRNA specific for a ChAT-mRNA target sequence identical in the rat and mouse and which allows almost complete silencing of ChAT fused to the EGFP reporter protein.

Inventors designed a lentiviral vector, LV-ChAT-shRNA, which produces both this shRNA and EGFP as a marker of tranduced cells, and they demonstrated that the vector causes dose-dependent knockdown of the endogenous expression of ChAT in cholinergic cells of the NG108-15 line. The maximal effect of this lentiviral vector used at $1.35 \times 10^5$ TU (ChAT inhibition>90%) was reached three days after infection. In contrast, a control lentiviral vector producing a shRNA with a scrambled sequence was ineffective to reduce ChAT expression. Next, they used the LV-ChAT-shRNA vector to target a cholinergic nucleus in adult rat brain: the medial septum. Inventors demonstrated that it successfully and specifically inhibits ChAT gene expression in this structure. The lentiviral vector is therefore effective for mouse (NG108-15) and rat ChAT, and is a powerful tool for silencing of ChAT in cholinergic cells both in culture and in vivo.

Using this methodology to analyze the consequences of specific impairment of cholinergic neurotransmission in given brain areas should lead to a better understanding of the functional role of acetylcholine. This is the first example of the knockdown of a gene specific to the cholinergic presynaptic system that can be applied to rat and mouse animal models.

ChAT is considered to be a relatively stable protein. Its turnover rate has been studied by various approaches. The half-life of purified rat ChAT was estimated to be about five days under steady state conditions (Wenthold and Mahler, 1975). Tandon et al. (1996) analyzed the effects of colchicine on cat sympathetic preganglionic axons, and calculated that the half-life of ChAT in vivo is approximately four days. Hersh (1992) blocked ChAT synthesis with cycloheximide and deduced that the half-life of ChAT is greater than 24 hours in NG108-15 cells. Inventors temporal analysis of ChAT expression in NG108-15 cells infected with LV-ChAT-shRNA revealed that suppression of ChAT activity was maximal and quasi complete 72 h post-infection. Thus, the preexisting pool of ChAT fully decayed three days post-infection; 24 hours after infection, ChAT expression was already reduced to about 50% of the control value (FIG. 4D, 4E). This suggests that in NG108-15 cells, the half-life of ChAT is shorter than 24 hours.

Identification of accessible RNAi target sites is a critical step in the use of RNAi. Target sites for efficient RNAi can be found throughout the length of transcripts including the 5' and 3' UTR. To find an efficient siRNA, inventors screened several candidate sequences specific for various positions within the coding region of the ChAT transcripts. These sequences were chosen on the basis of empirical criteria using a common list of guidelines. However, their efficacy for RNAi was variable, even for those targeting neighboring sequences, such as the sequences E and F (Table 1; FIG. 3A, 3B). The mechanisms mediating this variability may involve RNA structure, steric obstruction due to RNA binding proteins or internal stability profiles of the siRNA (Khvorova et al., 2003). In the case of ChAT, the siRNA which exhibited the greatest silencing activity corresponds to a sequence near the 3'-end of the coding region. These various observations emphasize the value of testing multiple sites to find the optimal siRNA target.

To knock down endogenous neuronal gene expression in the brain, siRNAs can be delivered in several ways. Single or short-term application of synthetic siRNAs in a given brain region results in only a transient RNAi effect in even the best case (Makimura et al., 2002; Akaneya et al., 2005; Isacson et al., 2003) and thus is not suitable for persistent gene silencing. Chronic intracerebroventicular infusion of siRNA for two weeks can lead to a stable down regulation of a neuronal protein, as shown for the dopamine or the serotonin transporters (Thakker et al., 2004; 2005). This approach requires high doses of siRNA, targets many brain regions simultaneously and therefore leads to a widespread knock down. It is thus more pertinent for studying the general function of newly identified genes or broadly expressed genes, than for the functional investigation of genes in specific nuclei.

These constraints on the use of synthetic siRNAs have been herein overcome by inventors by the preparation of DNA vector-based systems which allow intracellular expression of shRNAs in the areas of interest to which they are administered directly.

Plasmid vectors producing shRNA have a limited application due to their transient expression and their poor neuron transfection efficacy. In contrast, inventors herein demonstrate that viral vectors allow the delivery and stable expression of shRNAs. In particular, lentiviral vectors display a strong tropism for neurons and are advantageously usable for spatially restricted shRNA-mediated gene silencing. The present invention illustrates the potential of these vectors.

Inventors herein describe lentiviral vectors which express both a ChAT-specific shRNA and EGFP to facilitate the identification of transduced cells. They show that such a vector silences the endogenous expression of ChAT not only in cultured cholinergic cells but also in vivo in the cholinergic neurons of the rat medial septum. This strategy can be applied to other cholinergic brain regions and to other species. Moreover, it can be extended to other proteins required for cholinergic presynaptic function, including the high affinity choline transporter (CHT1), to inhibit choline uptake necessary for acetylcholine synthesis, and the vesicular acetylcholine transporter (VAChT), to block the vesicular translocation of the neurotransmitter.

An additional aspect of interest of lentiviral vectors is that they can be modified to allow the controlled expression of shRNAs (Amar et al., 2006; Wiznerowicz et al., 2006; Pluta et al., 2007). By using such vectors, it is possible to induce timed and specific ChAT silencing, to reverse its knockdown and to investigate time-dependent effects of ChAT reduction.

Plasmids and Lentiviral Vectors Construction and Production

Inventors constructed a plasmid expressing the rat ChAT protein fused to the enhanced green fluorescence protein (EGFP). The ChAT cDNA sequence was excised from the recombinant plasmid pSPT18 by EcoRI digestion (Brice et al., 1989) and inserted into the EcoRI site of the pEGFP-CI plasmid (Invitrogen), in-frame with the EGFP reporter gene. The expression of EGFP-ChAT is driven by a CMV promoter.

Potential siRNA sequences of 19nt specific to rat and mouse ChAT mRNAs (sequences A to G, Table 1) were selected empirically with a design tool incorporating standard parameters (Qiagen). DNA templates of 64 by were designed for the synthesis of each siRNA as described by Brummelkamp et al. (2002). Each contains the selected 19nt targeting sequence in both sense and antisense orientations separated by a 9nt spacer (5'-TTCAAGAGA-3') (SEQ ID NO: 64), followed by five thymidines as an RNA polymerase III transcription termination signal. BglII and HindIII restriction sites were incorporated at the 5' and 3' ends, respectively. These templates were synthesized chemically as two complementary DNA oligonucleotides (Eurogentech), annealed and inserted between the BglII/HindIII sites of the pSUPER vector (OligoEngine) downstream from the H1 promoter. The resulting 49nt-transcripts form a stem-loop structure, the shRNA, which is cleaved intracellularly to produce a 19nt RNA duplex with the characteristics of siRNAs (Elbashir et al., 2001). As controls for sequence specificity, pSUPER vectors producing a shRNA targeting the human ZNF-191 transcription factor (Olfa Khalfallah, unpublished results) and an RNA with a scrambled sequence (Sc) with the same base composition as the shRNA-G (sense sequence of the corresponding siRNA: 5'-UCGUCAUAGCGUGCAUAGGUU-3' (SEQ ID NO: 65) were constructed.

Lentiviral vectors were generated to produce the siRNA-G or the scrambled RNA as control. The complete shRNA expression cassettes (the H1 promoter plus the siRNA template) were excised from the corresponding recombinant pSUPER plasmids by ClaI and BamHI digestion. These cassettes were transferred into the modified plasmid pTRIP ΔU3-EGFP vector (kindly provided by Dr A. P. Bemelmans, CNRS UMR 7091, Paris) by substitution of a ClaI/BamHI fragment. This vector also expresses EGFP as a reporter gene under the control of the PGK promoter.

Plasmids were purified by Qiagen and all constructs were verified by sequencing before use.

TABLE 1

Candidate target sites for RNAi in the rat and mouse ChAT transcripts

| | SEQ ID NO: | Target sequences | Positions |
|---|---|---|---|
| A | 66 | 5'-CCUGAAGAGCAGUUCAGGA-3' | +142 |
| B | 67 | 5'-GCACUUCCAAGACACCAAU-3' | +348 |
| C | 68 | 5'-CUGGUGUGCUUAGCUACAA-3' | +398 |
| D | 69 | 5'-GUGAUCUGUUCACUCAGUU-3' | +659 |
| E | 70 | 5'-UAACCGGCAUGGCCAUUGA-3' | +1523 |
| F | 71 | 5'-GAGCCACCUGAGAUGUUCA-3' | +1588 |
| G | 72 | 5'-GAGCGAGCCUUGUUGACAU-3' | +1814 |

All these sequences are identical in rat and mouse ChAT-mRNAs. Their position is given relative to that of the translation initiation codon in the sequence of the rat ChAT transcripts (Brice et al., 1989). The translation stop codon is located at position 1933.

Cell Culture, Transfection and Transduction

The cell lines used in this study were 293T, derived from embryonic human kidney, and the mouse neuroblastoma×rat glioma hybrid NG108-15. Cells were cultured at 37° C. in a humidified chamber containing 5% $CO_2$. 293T cells were maintained in Dulbecco's Modified Eagle's Medium (DMEM, Gibco) supplemented with 10% heat-inactivated fetal calf serum (ATGC), 10000 U/ml penicillin and 10 mg/ml streptomycin. The NG108-15 cell line was maintained in DMEM supplemented with 10% fetal calf serum, 100 μM hypoxantin, 0.4 μM aminopterin, 16 μM thymidine, 100 mM sodium pyruvate, 4 mM glutamine, 10000 U/ml penicillin and 10 mg/ml streptomycin.

Transfections of 293T cells for testing the effectiveness of shRNAs-A to -G were performed with polyethylenimin (PEI, Aldrich). Twenty-four hours prior to transfection, cells were seeded in 60 mm-diameter culture dishes at a density of $3 \times 10^5$ cells/dish. The EGFP-ChAT plasmid (0.25 μg) and each pSUPER construct (2.3 μg) diluted in 100 μl DMEM were mixed with a solution of 4 μl PEI in 100 μl DMEM. The DNA/PEI mix was incubated for 15 min at room temperature, added to the cells for 4 h at 37° C. and removed. Cells were then grown in normal culture medium (described above) and harvested 24, 48 or 72 h later. Silencing efficiency was monitored by quantification of EGFP (see below).

For transduction experiments, $8 \times 10^4$ NG108-15 cells were mixed with the viral preparation in 200 μl of culture medium, seeded into 16 mm-diameter wells and incubated at 37° C. One hour after infection, 800 μl of culture medium was added and cells were returned at 37° C. Cells were cultured and passaged at the third and seventh days of culture.

Lentiviral Vector Production

Lentivirus vector particles were produced by calcium phosphate transient cotransfection of 293T cells by the vector plasmid, an encapsidation plasmid (p8.9), and a vesicular stomatitis virus (VSV) expression plasmid (pHCMV-G) as previously described (Zennou et al., 2001). The supernatants were treated with DNAse I (Roche Diagnostic) and subjected to ultracentrifugation. The resulting pellet was resuspended in PBS, aliquoted and frozen at −80° C. until use. The HIV p24 Gag antigen was quantified for each stock with an ELISA kit (Beckman Coulter, Villepinte, France). In addition, EGFP-expressing vectors were titered by infecting cells with serial dilutions of each lentiviral stock. The percentage of transduced cells, identified by EGFP fluorescence, was estimated by flow cytometry 72 h post-transfection and used to determine the number of transducing units (TU) per unit volume. The titers of the viral preparations used in the experiments described were: $9 \times 10^7$ and $5 \times 10^7$ TU/ml for LV-ChAT-shRNA and LV-Sc-shRNA, respectively (in vitro experiments), and $5 \times 10^8$ and $1 \times 10^8$ TU/ml for and LV-Sc-shRNA, respectively (in vivo experiments).

Assays

EGFP levels were determined by FACScan flow cytometer. Briefly, transfected or infected cells were collected, fixed in 2% paraformaldehyde/PBS and analyzed by fluorescence-activated cell sorting (FACS) by using a Becton Dickinson (Franklin Lakes, N.J., USA) with excitation/emission filters at 488/507 nm.

ChAT activity was measured as described by Fonnum (1975) using [$^3$H]Acetylcoenzyme A (4.4 Ci/mmol, Amersham) as a substrate. Activity was determined in homogenates obtained by vortexing cells in the presence of 0.2 M NaCl/0.2% (v/v) Triton X-100. Each assay was done in duplicate. Proteins were assayed by the method of Bradford (1976) using bovine serum albumin as standard. ChAT specific activity is expressed as cpm/min/μg proteins.

Animals and Surgery

Adult Sprague-Dawley male rats (220 g; Janvier Laboratories) were housed in a humidity- and temperature-controlled room with 12 h light/12 h dark cycles (light onset at 7:00 AM). Food and water were provided ad libidum. Experiments were performed in accordance with the Centre National de la Recherche Scientifique (CNRS) guidelines for the care and use of laboratory animals.

Rats were anesthetized with intraperitoneal injections of 50% ketamine/50% rompun (v/v) and positioned in a stereotaxic apparatus (Kopf Instruments, CA, USA).

Lentiviral vectors were injected into nine sites in the medial septal area at the following coordinates relative to the bregma (1) anteroposteriority (AP): +0.3 mm; laterality (L): −0.2 mm; ventrality (V): −6.8 mm; −6.4 mm; −6 mm; (2) AP: +0.3 mm; L: +0.2 mm; V: −6.8 mm; −6.4 mm; −6 mm; (3) AP: +0.8 mm; L: 0 mm; V: −7.2 mm; −6.8 mm; −6.4 mm (Paxinos and Watson, 1982). One microliter of lentiviral vector preparation or PBS was injected into each site at a rate of 0.25 µl/min through a 10 µl. Hamilton syringe driven by a CMA/100 microinjection pump. Following virus delivery, the needle was left in place for 4 min and then slowly withdrawn from the injection site.

For histological analysis, rats were deeply anesthetized with pentobarbital and perfused with 0.9% NaCl (50 ml) followed by 4% paraformaldehyde/PBS (400 ml). Brains were removed, post-fixed for 2 h at 4° C. in the same fixative, cryoprotected in 15% sucrose/PBS and frozen. Serial sections were cut (20 µm) and mounted onto gelatin-coated slides.

Immunohistochemistry Analysis and Cell Counting

Double labeling for ChAT and EGFP was performed by immunofluorescence. Sections were incubated overnight at 4° C. with simultaneously a goat polyclonal anti-ChAT antibody (1:50; Millipore) and a mouse monoclonal anti-GFP antibody (1:1000; Abcam, Cambridge, UK) in 5% normal donkey serum/0.5% Triton X-100/0.01M PBS. ChAT and EGFP immunostainings were visualized with Alexa-555 donkey anti-goat and Alexa-488 donkey anti-mouse secondary antibodies (Invitrogen), respectively.

For staining of the vesicular acetylcholine transporter (VAChT), sections were incubated for 30 min at room temperature with 10% normal horse serum/0.2% Triton (Sigma)/PBS, then overnight at 4° C. with a goat polyclonal anti-VAChT antibody (1:25, Promega) diluted in 1% normal horse serum/0.2% Triton (Sigma)/PBS. Sections were then treated for 1 h at room temperature with a goat biotinylated secondary antibody (Vector laboratories, Burlingame, Calif., USA) then with avidin-biotin-peroxidase complex reagents (ABC; Vector Laboratories, Burlingame, Calif., USA). The immunoreactions were visualized using 3,3-diaminobenzidine (Vector Laboratories) as a chromogen.

Sections were analyzed using a Leica microscope and images acquired with a Leica DFC 300FX camera and associated software.

Quantification of ChAT-expressing cells in the medial septum (MS) was carried out by using a Leica microscope (10× objective). For each rat brain, countings were performed on every $8^{th}$ frontal section over the entire extend of the MS. A mean of 7 sections was analyzed per rat. On each section, the total number of ChAT-positive neurons within the MS area were counted manually. Particular care was taken to perform the counts in slices corresponding to the same level of the MS in LV-ChAT-shRNA, LV-Sc-shRNA and PBS injected brains. The numbers of ChAT-positive neurons were summed and the ratios LV-ChAT-shRNA/PBS and LV-Sc-shRNA/PBS were calculated.

Selection of a ChAT-mRNA Target Sequence Efficient for RNAi

Inventors first identified an interfering sequence for selective silencing of ChAT. No precise sets of rules have yet been established to select target sequences for efficient RNAi. Thus, to choose potential target sites in the ChAT-mRNA sequence, inventors used a selection algorithm based on empirical criteria, to which they added further constraints. ChAT is encoded in mammals by several mRNAs which differ in their 5' non coding sequences (Misawa et al., 1992; Kengaku et al., 1993), so that only the coding and the 3' untranslated regions of the ChAT transcripts were considered. Inventors wanted to be able to knockdown ChAT expression in the rat and the mouse, so that only sequences that are identical in the two species were taken into account. Also, each candidate sequence had to be strictly specific to ChAT transcripts. A panel of seven sequences of 19nt was selected, at different positions within the coding region of ChAT mRNA (Table 1). Analysis by BLAST research revealed that none of them displays a significant sequence identity with any other mRNA.

Inventors next examined the capacity of these candidate sequences, designated A to G, to silence ChAT expression. For intracellular expression of siRNAs, seven pSUPER-derived plasmids were designed, in which the synthesis of the shRNAs is driven by an H1 polymerase III promoter (see above). An irrelevant plasmid which produces a shRNA specific to the human transcription factor ZNF-191 was also constructed and used as control for silencing specificity.

These constructs were then tested for their ability to disrupt the production of an EGFP-ChAT fusion protein. Non cholinergic 293T cells were transiently co-transfected with each shRNA-producing construct and with a plasmid expressing rat ChAT fused to the EGFP reporter protein. The proportion of cells which exhibit EGFP fluorescence was quantified by flow cytometry. The difference in fluorescence between cells transfected with pSUPER plasmids with and without insert reflects the extent of inhibition of EGFP-ChAT expression and thus the efficacy of the ChAT-targeting shRNAs. Each of the ChAT-specific shRNA constructs markedly reduced the number of EGFP-ChAT expressing cells (FIG. 3A, 3B). However, one day after transfection, shRNAs-A to -G were not equally effective (range 19% to 99%). These differences were lower 48 h after transfection, by which time EGFP fluorescence was reduced by at least 70% by each sequence. For most constructs, the effect was maximal 48 h post-transfection, but for sequence G the greatest effect was 24 h after transfection. In contrast, the ZNF191-shRNA failed to silence EGFP-ChAT expression, confirming the specificity of the effect of the ChAT-targeted shRNAs. The overall decrease in the proportion of fluorescent cells in control conditions between 48 and 72 h post-transfection most probably results from cell proliferation.

The most pronounced knockdown was obtained with shRNA-G, which blocked EGFP expression by about 99% within 24 h of transfection. To examine the specificity of its effect, a shRNA with a scrambled (Sc) sequence corresponding to shRNA-G, and which matches no sequence in the rat and mouse genomes, was designed and inserted into the H1 promoter-containing pSUPER plasmid. shRNA-Sc did not display ChAT silencing activity as assessed by co-transfection of 293T cells in the same conditions as above (FIG. 3C, 3D).

Therefore, the sequence G, which was the most effective target for RNAi, and its corresponding scrambled control sequence (Sc), were used for further experiments.

Knockdown of Endogenous ChAT Expression in Cultured Cholinergic Cells

For long-term silencing of ChAT expression in cholinergic cells in vitro and in vivo, inventors generated a recombinant lentiviral vector, named LV-ChAT-shRNA, which expresses the shRNA-G. They also constructed the corresponding control vector, designated LV-Sc-shRNA, which produces the shRNA-Sc. These vectors also encode EGFP allowing detection of transduced cells. Their general structure is shown on FIG. 4A.

Inventors tested whether LV-ChAT-shRNA represses endogenous ChAT synthesis in the cholinergic cell line NG108-15. These cells produce and release acetylcholine, and express ChAT, VAChT and muscarinic receptors. They have been extensively used to study cholinergic neurotransmission and ChAT gene properties (Hamprecht, 1977; Rosenberg et al., 1978; Misawa et al., 1992; De Gois et al., 2000).

NG108-15 cells were infected with increasing amounts of LV-ChAT-shRNA or the control vector LV-Sc-shRNA. Ten days after infection, the silencing of ChAT expression was assessed by assaying its enzymatic activity. Infection with the LV-ChAT-shRNA vector caused a substantial and dose-dependent reduction of ChAT activity (FIG. 4B). ChAT expression decreased with viral dose until $0.5 \times 10^5$ TU, a dose at which ChAT expression was inhibited by ≈95%. The dramatic decrease of ChAT activity did not result from a toxic effect of the lentiviral vector: FACS analysis indicated that the number of EGFP-expressing cells also increased with the viral dose (FIG. 4C). In contrast, identical titres of the lentiviral LV-Sc-shRNA vector did not decrease ChAT activity, indicating that the inhibition of ChAT expression by LV-ChAT-shRNA was specific (FIG. 4B).

Inventors performed a time course analysis to determine the lag before the RNAi mechanism begins to act. Cells were infected with equal amounts of LV-ChAT-shRNA or LV-Sc-shRNA and harvested at various times post-infection (FIG. 4D, 4E). One day after infection, ChAT activity was more than 50% lower in LV-ChAT-shRNA transduced cells than in LV-Sc-shRNA transduced cells. The maximal effect of LV-ChAT-shRNA was three days after infection, when ChAT activity was about 8% of that in LV-Sc-shRNA-infected cells. Thereafter, ChAT knockdown in continuously dividing cells remained substantial (about 80%). Thus RNAi-mediated ChAT suppression is triggered rapidly following infection by LV-ChAT-shRNA.

These experiments demonstrate that intracellularly produced shRNA generated by the lentiviral vector LV-ChAT-shRNA successfully knocks down endogenous ChAT expression in cholinergic cells in culture.

Knockdown of Endogenous ChAT Expression in the Brain

Inventors then investigated whether LV-ChAT-shRNA silences ChAT expression in particular cholinergic structures in the brain and can therefore be used to inactivate cholinergic neurons in vivo. Inventors focused this study on the cholinergic neurons of the medial septum (MS), which innervate the hippocampus and degenerate at early stages of Alzheimer's disease. The lentiviral vectors LV-ChAT-shRNA and LV-Sc-shRNA or PBS were delivered by stereotaxic injection into the MS area of adult rats.

The expression of EGFP and ChAT was analyzed by double immunofluorescence two weeks after injection. In LV-Sc-shRNA-injected brains, co-expression of EGFP and ChAT in MS cells demonstrates that the vectors that express shRNAs and EGFP had transduced septal cholinergic neurons, and that ChAT expression is maintained in neurons infected with LV-Sc-shRNA (FIG. 5B, 5D).

In contrast, ChAT expression was strongly reduced in neurons transduced by LV-ChAT-shRNA in the MS (FIG. 5A, 5C). In LV-ChAT-shRNA injected brains in which EGFP is expressed over the entire extend of the MS, the number of neurons containing ChAT was reduced by 67 to 87%, with a means of 79.6±2.2% (n=9) relatively to control brains injected with PBS (not shown). Moreover, LV-ChAT-shRNA failed to suppress the expression of another presynaptic cholinergic protein, VAChT, attesting its specificity towards ChAT transcripts (FIG. 5E) and the maintenance of cholinergic neuron integrity.

All together, these results demonstrate that the lentiviral vector expressing the shRNA-G specifically silences ChAT expression in vivo in the MS.

What is claimed is:

1. A nucleic acid sequence producing at least one functional micro RNA (miRNA), at least one functional short-hairpin RNA (shRNA), and/or at least one functional small interfering RNA (siRNA); said miRNA, shRNA, and/or siRNA being designed to silence the expression of a gene that encodes a cholinergic protein, choline acetyltransferase (ChAT); wherein the sense sequence of said nucleic acid sequence is 5'-GAGCGAGCCUUGUUGACAUUU-3' (SEQ ID NO: 13) and the antisense sequence of said nucleic acid sequence is 5'-AUGUCAACAAGGCUCGCUCUU-3' (SEQ ID NO: 14).

2. A virus vector comprising a nucleic acid sequence producing at least one functional micro RNA (miRNA), at least one functional short-hairpin RNA (shRNA), and/or at least one functional small interfering RNA (siRNA); said miRNA, shRNA, and/or siRNA being designed to silence the expression of a gene that encodes a cholinergic protein, choline acetyltransferase (ChAT); wherein the virus vector is a non-replicative lentivirus comprising a lentiviral genome; said lentivirus being pseudotyped for the selective transfer of the lentiviral genome into cells of the nervous system; wherein the sense sequence of said nucleic acid sequence is 5'-GAGCGAGCCUUGUUGACAUUU-3' (SEQ ID NO: 13) and the antisense sequence of said nucleic acid sequence is 5'-AUGUCAACAAGGCUCGCUCUU-3' (SEQ ID NO: 14).

3. The lentivirus according to claim 2, wherein the lentivirus is selected from the group consisting of Human Immunodeficiency Virus type 1 (HIV-1), Human Immunodeficiency Virus type 2 (HIV-2), Simian Immunodeficiency Virus (SIV), Feline Immunodeficiency Virus (FIV), Equine Infectious Anaemia Virus (EIAV), Bovine Immunodeficiency Virus (BIV), Visna Virus of sheep (VISNA) and Caprine Arthritis-Encephalitis Virus (CAEV).

4. The lentivirus according to claim 2, wherein the lentivirus is deprived of any lentiviral coding sequence and of the enhancer region of the U3 region of the LTR3'.

5. The lentivirus according to claim 2, wherein said lentivirus is pseudotyped with an envelope of a rhabdovirus.

6. The lentivirus according to claim 2, wherein the lentiviral genome comprises, between LTR3' and LTR5' sequences, a lentiviral ψ encapsidation sequence, a nucleic acid sequence producing at least one functional micro RNA (miRNA), at least one functional short-hairpin RNA (shRNA) and/or at least one functional small interfering RNA (siRNA), a promoter and optionally a sequence enhancing the nuclear import of the retrotranscribed viral DNA, a sequence enhancing RNA nuclear export, a transcriptional regulation element, a post-transcriptional regulatory element, and/or a mutated integrase gene.

7. The lentivirus according to claim 6, wherein the promoter is a viral promoter or a cellular promoter.

8. The lentivirus according to claim 7, wherein the promoter is a cellular promoter allowing expression of a shRNA, selected from the group consisting of H1, U6 and 7SK RNA polymerase III promoter.

9. The lentivirus according to claim 7, wherein the promoter is a viral promoter allowing expression of a miRNA, selected from the group consisting of CMV, TK, RSV LTR polymerase II promoter.

10. The lentivirus according to claim 7, wherein the promoter is a cellular promoter allowing expression of a miRNA, selected from the group consisting of PGK, Rho, EF1α, Thy1, ChAT, VAChT, CHT1, NSE, Nestin, S100β polymerase II promoters.

11. The lentivirus according to claim 6, wherein the promoter is a transactivator induced promoter that modulates RNA interference, said transactivator induced promoter comprising a plurality of transactivator binding sequences operatively linked to the nucleic acid sequence producing at least one functional micro RNA (miRNA), at least one functional short-hairpin RNA (shRNA) and/or at least one functional small interfering RNA (siRNA).

12. The lentivirus according to claim 11, wherein the transactivator is a tetracycline-dependent transactivator selected from the rtTA-Oct.2 transactivator composed of the DNA binding domain of rtTA2-M2 and of the Oct-2$^Q$(Q→A) activation domain, and the rtTA-Oct.3 transactivator composed of the DNA binding domain of the *E. coli* Tet-repressor protein and of the Oct-2$^Q$(Q→A) activation domain.

13. The lentivirus according to claim 6, wherein the promoter is a transactivator induced promoter that modulates RNA interference, said transactivator induced promoter comprising at least one transactivator binding sequence operatively linked to the nucleic acid sequence producing at least one functional micro RNA (miRNA), at least one functional short-hairpin RNA (shRNA) and/or at least one functional small interfering RNA (siRNA), and wherein the transactivator is selected from the group consisting of a tetR-KRAB-based transactivator, a tetR-VP16 transactivator and a rapamycin inducible transactivator.

14. The lentivirus according to claim 6, wherein the sequence enhancing the nuclear import of the retrotranscribed viral DNA is the lentiviral cPPT CTS (Flap) sequence.

15. The lentivirus according to claim 6, wherein the sequence enhancing the RNA nuclear export comprises the HIV-1 REV response element (RRE) sequence.

16. The lentivirus according to claim 6, wherein the sequence enhancing the RNA nuclear export comprises the CTE element.

17. The lentivirus according to claim 6, wherein the post-transcription regulation element is selected from the group consisting of Woodchuck hepatitis virus responsive element (WPRE), APP UTR5' region, TAU UTR3', and an insulator sequence selected from the group consisting of MAR, SAR, S/MAR, scs and scs' sequences.

18. The lentivirus according to claim 6, wherein the integrase comprises a mutation in at least one of its basic region and/or catalytic region responsible for the lentivirus to be non integrative.

19. A recombinant cell comprising a nucleic acid sequence producing at least one functional micro RNA (miRNA), at least one functional short-hairpin RNA (shRNA), and/or at least one functional small interfering RNA (siRNA); said miRNA, shRNA, and/or siRNA being designed to silence the expression of a gene that encodes a cholinergic protein, choline acetyltransferase (ChAT); wherein the sense sequence of said nucleic acid sequence is 5'-GAGCGAGCCUUGUUGA-CAUUU-3' (SEQ ID NO: 13) and the antisense sequence of said nucleic acid sequence is 5'-AUGUCAACAAG-GCUCGCUCUU-3' (SEQ ID NO: 14).

20. A kit for expressing a nucleic acid sequence producing at least one functional micro RNA (miRNA), at least one functional short-hairpin RNA (shRNA), and/or at least one functional small interfering RNA (siRNA); said miRNA, shRNA, and/or siRNA being designed to silence the expression of a gene that encodes a cholinergic protein, choline acetyltransferase (ChAT) and a notice comprising instructions for using the nucleic acid sequence; wherein the sense sequence of said nucleic acid sequence is 5'-GAGCGAGC-CUUGUUGACAUUU-3'(SEQ ID NO: 13) and the antisense sequence of said nucleic acid sequence is 5'-AUGUCAA-CAAGGCUCGCUCUU-3' (SEQ ID NO: 14).

* * * * *